(12) United States Patent
Auerbach-Nevo et al.

(10) Patent No.: US 12,351,843 B2
(45) Date of Patent: Jul. 8, 2025

(54) METHOD FOR PURIFYING AND QUANTIFYING THROMBIN AND ITS DEGRADATION POLYPEPTIDES

(71) Applicant: Omrix Biopharmaceuticals Ltd., Rehovot (IL)

(72) Inventors: Tamar Auerbach-Nevo, Rehovot (IL); Nadav Orr, Mazkeret Batia (IL); Israel Nur, Rehovot (IL)

(73) Assignee: Omrix Biopharmaceuticals Ltd., Kiryat-Ono (IL)

( * ) Notice: Subject to any disclaimer, the term of this patent is extended or adjusted under 35 U.S.C. 154(b) by 664 days.

(21) Appl. No.: 17/472,737

(22) Filed: Sep. 13, 2021

(65) Prior Publication Data

US 2021/0403892 A1 Dec. 30, 2021

Related U.S. Application Data

(62) Division of application No. 16/712,207, filed on Dec. 12, 2019, now Pat. No. 11,149,263, which is a division of application No. 15/922,301, filed on Mar. 15, 2018, now Pat. No. 11,008,560, which is a division of application No. 15/051,821, filed on Feb. 24, 2016, now Pat. No. 10,066,224.

(60) Provisional application No. 62/120,510, filed on Feb. 25, 2015.

(30) Foreign Application Priority Data

Feb. 25, 2015 (IL) .......................................... 237416

(51) Int. Cl.
| | | |
|---|---|---|
| *C12N 9/74* | (2006.01) | |
| *C07K 14/745* | (2006.01) | |
| *C12Q 1/56* | (2006.01) | |
| *G01N 33/49* | (2006.01) | |
| *A61K 38/00* | (2006.01) | |

(52) U.S. Cl.
CPC .......... *C12N 9/6429* (2013.01); *C07K 14/745* (2013.01); *C12Q 1/56* (2013.01); *G01N 33/491* (2013.01); *A61K 38/00* (2013.01); *C12Y 304/21005* (2013.01); *G01N 2333/96463* (2013.01)

(58) Field of Classification Search
None
See application file for complete search history.

(56) References Cited

U.S. PATENT DOCUMENTS

| | | | |
|---|---|---|---|
| 4,965,203 A | 10/1990 | Silbering | |
| 5,142,838 A | 9/1992 | Simpson et al. | |
| 5,143,838 A | 9/1992 | Kraus | |
| 5,354,682 A * | 10/1994 | Kingdon | C12Y 304/21005 530/384 |
| 5,506,127 A | 4/1996 | Proba | |
| 5,831,003 A | 11/1998 | Baumbach et al. | |
| 6,121,232 A | 9/2000 | Nur et al. | |
| 7,125,569 B2 | 10/2006 | Nur | |
| 2009/0101809 A1 | 4/2009 | Wilbert | |
| 2009/0137001 A1 | 5/2009 | Onchi | |
| 2016/0244739 A1 | 8/2016 | Auerbach-Nevo et al. | |

FOREIGN PATENT DOCUMENTS

| | | |
|---|---|---|
| CN | 1587400 A | 3/2005 |
| CN | 1844380 A | 10/2006 |
| CN | 102239175 A | 11/2011 |
| CN | 104109202 A | 2/2017 |
| EP | 0443724 A1 | 8/1991 |
| EP | 0796623 A3 | 5/2000 |
| EP | 1390485 | 10/2006 |
| EP | 1939283 A4 | 2/2009 |
| JP | H10150980 A | 6/1998 |
| WO | 9833533 A1 | 8/1998 |
| WO | 0111952 A1 | 2/2001 |
| WO | 02095019 A1 | 11/2002 |
| WO | 2004103519 A3 | 2/2005 |
| WO | 2009032966 A1 | 3/2009 |

OTHER PUBLICATIONS

Ramazi, Shahin; Zahiri, Javad; "Post-translational modifications in proteins: resources, tools and prediction methods" Database, 2021 (Year: 2021).*
Seegers, Walter H; et al; "Preparation and Properties of Thrombin" Archives of Biochemistry and Biophysics, 128, 194-201, 1968 (Year: 1968).*
Butkowski, Ralph J; et al; "The Preparation and Activation of [sialyl-3H]Prothrombin" The Journal of Biological Chemistry, 249, 6562-6569, 1975 (Year: 1975).*
McDonald, K; et al; "The Oligosaccharide of Human Thrombin: Investigations of Functional Significance" Blood, 63, 188-194, 1983 (Year: 1983).*
Boissel, et al ., Covalent structures of B and Y Autolytic Derivatives Of Human-Thrombin, The Journal Of Biological Chemistry, 1984, pp. 5691-5697, vol. 259 Issue 9.
Braun, et al ., Preparation and characterization of proteolyzed forms of human-thrombin, Thrombosis Research, 1988, pp. 273-283, vol. 50 Issue 2.
Chang ., The structures and proteolytic specificities of autolysed human thrombin, Boichem, 1986, pp. 797-802, vol. 240 Issue 3.
Duncan, et al., Performance evaluation of non-porous versus porous ion-exchange packings in the separation of proteins by high-performance liquid Chromatography, Journal of Chromatography, 1987, pp. 3-12, vol. 397.

(Continued)

*Primary Examiner* — David W Berke-Schlessel
(74) *Attorney, Agent, or Firm* — David R. Crichton

(57) ABSTRACT

Provided is a method for purifying α-thrombin and for quantifying α-thrombin and its degradation polypeptides in a liquid proteinatious solution. The method employs a one-step anion exchange chromatography method. The method allows purification and/or quantification of a homogenous post-translationally modified α-thrombin. The method can also be used for purification and/or quantification of β-thrombin.

4 Claims, 8 Drawing Sheets

(56) References Cited

OTHER PUBLICATIONS

Hermanson, et al ., Immobilized Affinity Ligand Techniques, Academic Press Inc, 1992, pp. 1-45, Page Number.
Yakuhin Kenkyu, Studies on the Quality of Enzyme Preparation (VIII) Thrombin Preparations, Yakuhin Kenkyu, 1989, pp. 784-789, vol. 20, No. 4.
Karlsson ., Analysis of human a-thrombin by hydrophobic interaction high-performance liquid chromatography, Protein Expression & Purification, 2003, pp. 171-174, vol. 27 Issue 1.
Kawasaki, et al ., Studies On the Quality of Enzyme Preparation (VIII) Thrombin Preparations, Yakuhin Kenkyn, 1989, pp. 784-789, vol. 20 Issue 4.
Kenney, et al ., Ion-Exchange Chromatography Of Proteins, Practical Protein Chromatography, 1992, pp. 1-12, vol. 11 Issue 16.
Khan ., The Role of Ion Exchange Chromatography in Purification and Characterization of Molecules, Ion Exchange Technologies, 2012, pp. 331-342, Chapter 14.
Kroner, et al., Systematic generation of buffer systems for pH gradient ion exchange chromatography and their application, Journal Of Chromatography, Feb. 7, 2013, pp. 78-87, vol. 1285.
Lundblad, et al ., Preparation and partial characterization of two forms of bovine thrombin, Biochemical and Biophysical Research Communication, 1975, pp. 482-489, vol. 66 Issue 2.
Parkins, et al ., The formulation of biopharmaceutical products, PSTT, 2000, pp. 129-137, vol. 3 Issue 4.
Shan, et al., Gradient chromatofocusing .versatile ph gradient separation of proteins in Ion-exchange HPLC: Characterization studies, Analytical Chemistry, Nov. 1, 2002, pp. 5641-5649, vol. 74 Issue 21.
Sola, et al ., Glycosylation of Therapeutic Proteins: An Effective Strategy to Optimize Efficacy, BioDrugs, 2010, pp. 9-21, vol. 24 Issue 1.
Tosoh Research, TSL-GEL STAT, Tosoh Research & Technology Review, 2008, pp. 103-107, vol. 52.
Wendeler, et al ., Process-scale purification and analytical characterization of highly gamma-carboxylated recombinant human prothrombin, Journal of chromatography, 2013, pp. 171-178, vol. 1325.
"Fibrin Sealant Kit Fibrini Glutinum", European Pharmacopoeia, No. 0903, pp. 857-858, 1997.
Berg et al., "The Isoelectric Point of Thrombin and its Behaviour Compared to Prothrombin at Some Solid Surfaces", of Thrombosis and Haemostasis, vol. 42, pp. 972-982, 1979.
Fekete et al., "Modern Column Technologies for the Analytical Characterization of Biopharmaceuticals in Various Liquid Chromatographic Modes", Advances in Biopharmaceutical Analysis, pp. 8-15, Oct. 2015.
International Search Report and Written Opinion, received for PCT Application No. PCT/IL2016/000004, mailed on May 24, 2016, 15 pages.

* cited by examiner

METHOD FOR PURIFYING AND QUANTIFYING THROMBIN AND ITS DEGRADATION POLYPEPTIDES

CROSS REFERENCE TO RELATED APPLICATION

This application is a divisional of co-pending U.S. application Ser. No. 16/712,207 filed Dec. 12, 2019, which is divisional of U.S. application Ser. No. 15/922,301 filed Mar. 15, 2018, now U.S. Pat. No. 11,008,560, which is a divisional of U.S. application Ser. No. 15/051,821, filed Feb. 24, 2016, now U.S. Pat. No. 10,066,224, which claims the benefit of provisional application No. 62/120,510 filed Feb. 25, 2015 and claims priority from Israeli Patent Application 237416 filed Feb. 25, 2015 the disclosure of which is hereby incorporated by reference in its entirety.

FIELD OF THE INVENTION

Provided is a method that allows analyzing and quantifying α-thrombin, homogenously glycosylated α-thrombin and/or thrombin degradation polypeptides in liquid proteinatious solutions. In particular, provided is an analytical and quantitative method that employs a single chromatographic step. Also, provided is a method that allows efficient and robust purification of α-thrombin and/or homogenously glycosylated α-thrombin without thrombin degradation polypeptides. The invention can also be used for purification and/or quantification of β-thrombin.

BACKGROUND OF THE INVENTION

Thrombin is a serine protease which is widely used in clinical applications in several commercial products. It is a common component of surgical dressings, and has been used in combination with fibrinogen and other proteins in hemostatic systems such as fibrin glues, adhesives, and sealants. Fibrin sealants typically comprise a fibrinogen component and a thrombin component. When both components are mixed (e.g. when applied to a bleeding wound or surgical incision) thrombin cleaves the fibrinogen peptides off the fibrinogen thus allowing the latter to generate insoluble fibrin polymers/sealant.

Concentrated (e.g. more than 500 IU/mL), purified thrombin in aqueous liquid form may display a reduction in activity during prolonged storage, primarily as a result of autolysis. Assessment of thrombin degradation is thus an essential physico-chemical analytical tool for determining thrombin stability.

Mammalian α-thrombin is made up of two disulfide linked polypeptide chains A and B. The B chain is post-translationally modified (e.g. by glycosylation) and exhibits thrombin's proteolytic activity toward fibrinogen and other proteins. The α-thrombin can autolyze into β-thrombin, and γ-thrombin polypeptide derivatives, which can be partially identified by Gel electrophoresis and Western Blot.

Thrombin autolysis is a major challenge in manufacturing and storing of thrombin, especially at high concentrations. The methods known in the art for identifying thrombin degradation polypeptides (β-thrombin and γ-thrombin derivatives) are inadequate in that they either provide insufficient separation between thrombin and its degradation polypeptides, a denaturing separation and/or are labor intensive. Therefore, the quantitation is not accurate and/or possible.

Background art includes:
Boissel J P et al. "Covalent structures of beta and gamma autolytic derivatives of human alpha-thrombin". J Biol Chem. 1984 May 10; 259(9):5691-5697; Chang J Y. "The structures and proteolytic specificities of autolysed human thrombin". Biochem J. 1986 Dec. 15; 240(3):797-802; Karlsson G. "Analysis of human alpha-thrombin by hydrophobic interaction high-performance liquid chromatography". Protein Expr Purif. 2003 January; 27(1):171-174; European Patent No. EP 0443724; and WO 2004/103519.

Boissel et. al. describes the use of CEX-HPLC followed by RP-HPLC analysis to separate the different thrombin degradation polypeptides. Chang describes HPLC analysis of pure thrombin fractions separated by SEC chromatography and further analyzed using RP-HPLC. The above methods have the shortcoming of requiring at least two separation steps for quantification and separation of thrombin from other proteins.

Karlsson describes hydrophobic interaction chromatography (HIC) to separate thrombin degradation products.

European Patent No. EP 0443724 discloses a method for preparing a viral safe thrombin, however, the method is denaturing and shows no separation between the different thrombin degradation products or between the different α-thrombin post-translational variants.

WO 2004/103519 discloses methods for the separation of charged molecules such a proteins according to their isoelectric points (pI's) and includes the systems and buffering compositions employed for isolating charged molecules.

There remains an unmet need for analytical methods for quantifying α-thrombin or β-thrombin; and for the purification of active, intact α-thrombin or of β-thrombin from proteinatious solutions which overcome the above defects of the art.

SUMMARY OF THE INVENTION

Provided is a one-step chromatographic method for quantifying α-thrombin and/or homogenous post-translationally modified α-thrombin in a solution, the solution comprising the α-thrombin and at least one of an α-thrombin degradation polypeptide (β-thrombin and/or γ-thrombin polypeptide), post-translationally modified α-thrombin species or another protein.

Also, provided are methods for purifying α-thrombin from proteinatious solutions by providing good separation of intact e.g. non-degraded, functional, active α-thrombin and/or homogenous post-translationally modified α-thrombin, the solutions comprising the α-thrombin and at least one of an α-thrombin degradation polypeptide (β-thrombin and/or γ-thrombin polypeptide), post-translationally modified α-thrombin species or another protein.

Also, provided are methods for purifying a homogenous α-thrombin glycoform from a solution comprising heterogeneous glycosylated α-thrombin species.

Also, provided are methods for purifying and/or quantifying β-thrombin in a solution comprising the β-thrombin and at least one of α-thrombin e.g. post-translationally modified α-thrombin species, γ-thrombin or another protein.

As used herein, the term "at least one of" is both conjunctive and disjunctive in operation. For example, the expressions "at least one of A, B or C" means: A alone, B alone, C alone, A and B together, A and C together, B and C together, or A, B and C together.

Homogenous post-translationally modified α-thrombin can be homogenously glycosylated α-thrombin or homogenously glycosylated and homogenously sialylated α-thrombin.

A homogenous α-thrombin glycoform according to the instant application can be a "homogenously glycosylated α-thrombin" or "a homogenously glycosylated and homogenously sialylated α-thrombin species".

Typically, a glycoform is an isoform of a protein that differs only with respect to the number and/or type of attached glycans or polysaccharides. Glycoproteins often consist of a number of different glycans, with alterations in the attached saccharides.

Often, the terms "glycan" and "polysaccharide" refer to the carbohydrate portion of a glycoconjugate, such as a glycoprotein. Glycans can be homo- or hetero-polymers of monosaccharide residues, and can be linear or branched. The glycans can carry saccharides with or without negative charges.

The methods comprise: contacting the solution with an Anion Exchanger. The methods allow getting a robust and reproducible performance, providing highly purified and active α-thrombin and/or homogenous post-translationally modified α-thrombin; and accurate quantification of α-thrombin, homogenous post-translationally modified α-thrombin and/or its degradation polypeptides. The method also enables the quantification and/or purification of β-thrombin stand-alone.

In one aspect, provided is a method for purifying α-thrombin from a solution comprising the α-thrombin and at least one of an α-thrombin degradation polypeptide or another protein, the method comprising the steps of: 1-contacting the solution with an anion exchanger; 2-separating the α-thrombin from the at least one of the α-thrombin degradation polypeptide (e.g. from β-thrombin and/or γ-thrombin polypeptide) and/or the another protein by an anion exchange chromatography (AEX) using differential elution conditions; and 3-collecting an α-thrombin fraction, thereby obtaining purified α-thrombin.

In some embodiments, the method comprises separating the α-thrombin from the at least one of the α-thrombin degradation polypeptide (e.g. β-thrombin and/or γ-thrombin polypeptide) and the another protein by an anion exchange chromatography (AEX) using differential elution conditions.

In one embodiment, the α-thrombin is from a human blood or plasma source. In another embodiment, the α-thrombin is from a recombinant source.

The term "separating" used herein typically refers to isolating a specific compound from a solution comprising the specific compound and other compounds.

In one aspect, provided is a method for purifying homogeneously glycosylated α-thrombin from a solution comprising heterogeneously glycosylated α-thrombin, the method comprising the steps of: 1-contacting the solution with an anion exchanger; 2-separating the homogeneously glycosylated α-thrombin from the heterogeneously glycosylated α-thrombin by an anion exchange chromatography (AEX) using differential elution conditions; and 3-collecting a homogeneously glycosylated α-thrombin fraction, thereby obtaining purified homogeneously glycosylated α-thrombin.

In one aspect, provided is a method for purifying homogeneously glycosylated α-thrombin from a solution comprising heterogeneously glycosylated α-thrombin and at least one of an α-thrombin degradation polypeptide or another protein. In another aspect, provided is a method for purifying homogeneously glycosylated α-thrombin from a solution comprising at least one of heterogeneously glycosylated α-thrombin, an α-thrombin degradation polypeptide or another protein. The method comprising the steps of: 1—contacting the solution with an anion exchanger; 2—separating the homogeneously glycosylated α-thrombin by an anion exchange chromatography (AEX) using differential elution conditions; and 3—collecting a homogeneously glycosylated α-thrombin fraction, thereby obtaining purified homogeneously glycosylated α-thrombin.

In some embodiments after step 1— the contacting step, a washing step is carried out using an isocratic buffer/solution.

In one embodiment of the invention, the method comprises the steps of: loading the thrombin containing solution to an anion exchanger; washing with an isocratic solution; discarding the washed fraction; and eluting a desired α-thrombin fraction using a non-isocratic solution such as a pH gradient. Use of an isocratic solution typically relates to the use of a constant-composition mobile phase in liquid chromatography.

"A desired α-thrombin fraction" typically refers to any α-thrombin present in a solution for which purification and/or quantification is intended for, including, for example, homogeneous post-translationally modified α-thrombin e.g. homogeneously glycosylated α-thrombin or homogeneously glycosylated and homogeneously sialylated α-thrombin.

In one aspect, provided is a method for purifying a homogenous α-thrombin glycoform from a solution comprising heterogeneous glycosylated α-thrombin species, the method comprising the steps of:
  contacting the solution with an anion exchanger;
  separating the homogenous α-thrombin glycoform from the heterogeneous species by anion exchange chromatography using differential elution conditions, and
  collecting a homogenous α-thrombin glycoform fraction, thereby obtaining purified homogenous α-thrombin glycoform.

In one embodiment, the method also comprises the step of quantifying the purified homogenous α-thrombin glycoform.

In another aspect, provided is a one-step or single step chromatographic method for quantifying α-thrombin in a solution comprising the α-thrombin and at least one of an α-thrombin degradation polypeptide or another protein, the method comprising the steps of: separating the α-thrombin from the at least one of the α-thrombin degradation polypeptide or the another protein on anion exchange chromatography by differential elution conditions; collecting an α-thrombin fraction; and quantifying the α-thrombin. In another aspect, provided is a one-step or single step chromatographic method for quantifying α-thrombin in a solution comprising the α-thrombin and at least one of an α-thrombin degradation polypeptide or another protein, the method comprising the steps of: contacting the solution with an anion exchanger; separating the α-thrombin from the at least one of the α-thrombin degradation polypeptide or the another protein on anion exchange chromatography by differential elution conditions such as a pH gradient; collecting an α-thrombin fraction; and quantifying the α-thrombin.

In some embodiments, the α-thrombin is from a mammalian e.g. human or pig plasma source or a recombinant protein.

The chromatographic methods disclosed herein can be carried out using all techniques known to the person skilled in the art. For example, a High-Performance Liquid Chromatography device; a Fast Protein Liquid Chromatography (FPLC) and/or a stand-alone column with or without a connected detector can be employed.

In one embodiment, an Anion Exchange High-Performance Liquid Chromatography method is used. High-performance liquid chromatography (HPLC; also referred to as high-pressure liquid chromatography), is typically a technique that relies on pumps to pass a pressurized liquid solvent containing the sample mixture through a column filled with a solid adsorbent material. Each component in the sample interacts slightly differently with the adsorbent material, leading to the separation of the components. HPLC is distinguished from traditional ("low pressure") liquid chromatography because operational pressures are significantly higher (50-350 bar). Some models of mechanical pumps in a HPLC instrument can mix multiple solvents together in ratios changing in time, generating a composition gradient in the mobile phase. Various detectors are in common use, such as Ultra Violet (UV), photodiode array (PDA) or mass spectrometry. The detection can be carried out using UV absorbance detector at 190-400 nm ($A_{190\,nm}$-$A_{400\,nm}$). In one embodiment, when amines are included in the elution buffer, absorbance is measured at about $A_{280\,nm}$.

Typically, a chromatographic separation e.g. an HPLC run consists at least of the following steps: an equilibrated column is contacted e.g. loaded with a sample/mixture ("Loading"). After loading a washing step can be carried out. Following this step, the separated components are eluted from the column. This can be carried out isocratically (without changing the buffer composition as compared to the loading and/or equilibration steps) or through a gradient (changing at least one of the buffer characteristic, e.g. salt concentration, polarity, pH). In one embodiment, elution is carried out using a linear gradient. In the next step, the column can be regenerated ("Column regeneration"), meaning that the remaining components are given additional time at the highest concentration of the changed characteristic (salt concentration, polarity, pH) in order to elute from the column any remaining material. Regeneration can alternatively be carried out by changing other buffer characteristics (not changed during the elution step). The last step ("Column equilibration") can be an equilibration step, to allow the column to return to the original state in which the column is suitable for an additional use. The described steps can alternatively be carried out using an FPLC device and/or a stand-alone column. Chromatographic separation is well known in the art as described in Hidayat Ullah Khan (2012). The Role of Ion Exchange Chromatography in Purification and Characterization of Molecules, Ion Exchange Technologies, Chapter 14, 331-334. Advantageously, the methods according to the invention provide good peak separation of intact α-thrombin from its degradation polypeptides and/or from other proteins in the thrombin solution. Typically, in chromatographic methods "good separation"/"good peak separation" is considered an efficient separation of the components, in which the peaks detected, as representative of elution of the components, do not overlap; that is, the detector response returns to the base line level between the peaks. The term "good peak separation" is also meant to include "sufficient separation" in which a clear distinction between the eluting peaks appears, however, the detector response does not fully return to the base line level between the peaks.

Separation/resolution efficacy can be visually evaluated. Alternatively or in addition, the resolution (Rs), the extent to which a chromatographic column separates components from each other, can be mathematically defined: resolution is the difference between the peak retention times of a selected peak and the peak preceding it multiplied by a constant of 1.18, then divided by the sum of the peak widths at 50% of peak height. The term "retention time" refers to the interval between the instant of injection and detection of the peak apex (the most upper point of the peak) as representative of elution.

Generally, a resolution level of equal to or above 2 is considered as good separation of the component and allows good quantitation of the peak. A resolution of equal to or above 1.5 (and lower than 2) is considered as "sufficient separation" which enables separation and/or quantitation.

In one embodiment of the methods, the resolution between α-thrombin peaks and its degradation polypeptides is in the range of about 1.5 to about 8.

In one embodiment of the methods, the resolution between α-thrombin peaks and other proteins in the thrombin solution is higher than 8.

In one embodiment of the methods, the resolution between the different α-thrombin species peaks is in the range of about 1.5 to about 8.

In one embodiment, the resolution between the different α-thrombin degradation polypeptides (β-thrombin and γ-thrombin) is lower than 1.5 such as equal to 0. In one embodiment, β-thrombin and γ-thrombin elute in the same peak. In another embodiment, a certain β-thrombin form elutes in a separate peak e.g. the resolution between β-thrombin and other components in the solution is about 1.5 to about 8. Accordingly, in one aspect, the invention also provides a method for purifying β-thrombin from a solution comprising the β-thrombin and at least one of α-thrombin, γ-thrombin or another protein, the method comprising the steps of:

contacting the solution with an anion exchanger; separating the β-thrombin from the at least one of the α-thrombin, γ-thrombin and/or another protein by anion exchange chromatography using differential elution conditions; and collecting a β-thrombin fraction, thereby obtaining purified β-thrombin.

The term "β-thrombin fraction" typically refers to the fraction collected following elution of the loaded anion exchanger (e.g. loaded column) with a buffer under differential elution conditions.

In another aspect, the invention provides a one-step chromatographic method for quantifying β-thrombin in a solution comprising the β-thrombin and at least one of α-thrombin, γ-thrombin or another protein, the method comprising the steps of: contacting the solution with an anion exchanger; separating the β-thrombin from the at least one of the α-thrombin, γ-thrombin and/or the another protein on anion exchange chromatography by differential elution conditions; and quantifying the β-thrombin.

In some embodiments, the method further includes identifying the separated β-thrombin, α-thrombin and/or γ-thrombin containing fractions. In some embodiments, the method further includes quantifying α-thrombin and/or γ-thrombin.

In some embodiments, the method comprises separating the β-thrombin from the at least one of the α-thrombin, γ-thrombin and another protein by anion exchange chromatography using differential elution conditions.

In some embodiments, the chromatographic method is an anion exchange High-Performance Liquid Chromatography method. In some embodiments, the differential elution conditions comprise a pH gradient e.g. generated by using an eluent comprising of an amine or a mixture of amines. In some embodiments, the anion exchanger is made of non-porous particles.

In another aspect, the invention provides a purified β-thrombin obtainable by the methods of the invention; an isolated β-thrombin; and a formulation/kit comprising the purified/isolated β-thrombin as described herein.

In some embodiments, the method allows separating and collecting homogenous post-translationally modified α-thrombin fractions. In some embodiments, the homogenous post-translationally modification is homogenous glycosylation. In some embodiments, the homogenous post-translationally modification is homogenous glycosylation and sialylation. In some embodiments, the separated/collected α-thrombin fraction is a homogenous glycosylated α-thrombin. In some embodiments, the homogenous post-translationally modified α-thrombin is represented by a single glycoform. In some embodiments, the separated/collected α-thrombin glycoform is homogeneously glycosylated and/or homogeneously sialylated. In some embodiments, the homogeneity of the isolated, separated and/or collected post-translationally modified α-thrombin e.g. the homogenous α-thrombin glycoform is a level of at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99% or at least 100% identity. E.g. 50, 55, 60, 65, 70, 75, 80, 85, 90, 95, 99 or less than 100%, including any range between the disclosed percentages such as 50-55%, 50-60%, 50-65%, 50-70%, 50-75%, 50-80%, 50-85%, 50-90%, 50-95%, 50-99%, 50-100%, 55-60%, 55-65%, 55-70%, 55-75%, 55-80%, 55-85%, 55-90%, 55-95%, 55-99%, 55-100%, 60-65%, 60-70%, 60-75%, 60-80%, 60-85%, 60-90%, 60-95%, 60-99%, 60-100%, 65-70%, 65-75%, 65-80%, 65-85%, 65-90%, 65-95%, 65-99%, 65-100%, 70-75%, 70-80%, 70-85%, 70-90%, 70-95%, 70-99%, 70-100%, 75-80%, 75-85%, 75-90%, 75-95%, 75-99%, 75-100%, 80-85%, 80-90%, 80-95%, 80-99%, 80-100%, 85-90%, 85-95%, 85-99%, 85-100%, 90-95%, 90-99%, 90-100%, 95-99%, 95-100% identity. In yet another embodiment, the α-thrombin is un-modified, e.g. non-glycosylated.

In some embodiments, the proteinatious solution includes at least one of another protein, an α-thrombin degradation polypeptide (for example, β-thrombin polypeptide and/or γ-thrombin polypeptide), an α-thrombin that is not post-translationally modified (an unmodified α-thrombin), or post-translationally modified α-thrombin.

In some embodiments, the solution includes a mixture of unmodified and post-translationally modified α-thrombin.

In some embodiments, the solution includes heterogeneous post-translationally modified α-thrombin including different glycoform species of α-thrombin.

In some embodiments, the solution includes another protein or a protein fragment, which may be, for example, a protein that was added to the solution. In some embodiments, the protein is, for example, human serum albumin (HSA). In some embodiments of the method, the solution includes at least one of α-thrombin degradation polypeptide or another protein.

In some embodiments of the method, the solution includes at least one of α-thrombin degradation polypeptide or HSA.

In some embodiments of the method, the solution includes at least one of α-thrombin degradation polypeptide and HSA.

In some embodiments, the method comprises the step of: loading the solution onto an anion exchange column. In some embodiments, the method comprises contacting the solution with an anion exchanger in batch-wise form.

As used herein, "batch method", "batch-wise", and "batch form" generally refer to a technique in which a solution is contacted with a resin, typically in a single stage adsorption procedure. "A single stage adsorption procedure" refers to a procedure wherein all the components of the purification process (e.g. the resin and the solution) are incubated together e.g. in a stirred tank, batch reactor or a vessel, and the adsorption is carried out in a continuous manner. The resin-bound fraction can then be collected by an additional step of centrifugation and/or filtration.

In some embodiments, prior to contacting e.g. loading, the exchanger/column is equilibrated to a pH of 10.5 to about pH 7.0 (e.g. a pH of 9.1). The equilibration can be carried out using buffer or buffers suitable for equilibrating the exchanger at a pH of 10.5 to about pH 7.0 (e.g. a pH of 9.1).

In one embodiment, the buffer comprises a mixture of amines. In some embodiments, the amines mixture used for equilibration includes piperazine, triethanolamine, bis-tris propane, 1-methylpiperazine, bicine, bis-tris, diethanolamine, diethylamine, 1-histidine, imidazole, pyridine, tricine, triethanolamine, and/or tris.

In some embodiments, the amines mixture used for equilibration consists of piperazine, triethanolamine, bis-tris propane and 1-methylpiperazine. In some embodiments, the concentration of the amines in the equilibration buffer is in the range of about 1 to about 100 mM e.g. in the range of about 10 to about 20 mM or about 20 mM.

The flow rate during contacting e.g. loading can be in the range of about 0.1 to about 1.4 mL/minute. In some embodiments, the conditions for allowing separation between degradation polypeptides of α-thrombin, α-thrombin, homogenous α-thrombin glycoform and/or another protein includes applying differential elution conditions such as subjecting the anion exchanger/column to pH gradient conditions for elution.

In some embodiments, the differential elution conditions comprise applying a pH gradient e.g. stepwise or continuous (e.g. linear). Typically, a "continuous gradient" is defined as a gradient in which the eluent composition is changed gradually, continuously and constantly while the "stepwise gradient" includes instant changes in the eluent composition.

In some embodiments, the gradient length is in the range of 5 minutes to 100 minutes or 5 minutes to 60 minutes. In another embodiment, the gradient length is higher than 25 minutes e.g. higher than 30 or higher than 35 minutes. In some embodiments, the gradient length is in the range of higher than 25 minutes to 35 minutes or in the range of higher than 25 minutes to 30 minutes.

In one embodiment, elution is carried out with the same buffer used for equilibration of the anion exchanger.

In some embodiments, the linear pH gradient is from about pH 10.5 to about pH 2.0 such as in the range of about 9.1 to about pH 3.4.

In some embodiments, the pH gradient is generated using an eluent comprising of an amine or a mixture of amines. In some embodiments, the linear pH gradient is generated using an eluent buffer comprising a mixture of amines. In some embodiments, the amines mixture used during the differential elution conditions includes piperazine, triethanolamine, bis-tris propane, 1-methylpiperazine, bicine, bis-tris, diethanolamine, diethylamine, 1-histidine, imidazole, pyridine, tricine, triethanolamine, and/or tris. In some embodiments, the amines mixture used during the differential elution conditions consists of piperazine, triethanolamine, bis-tris propane and 1-methylpiperazine. In some embodiments, the concentration of each amine in the buffer is in the range of about 1 to about 100 mM. In some embodiments, the concentration of each amine in the buffer is about 20 mM.

In some embodiments, the linear pH gradient is generated using two eluent buffers comprising a mixture of amines. In some embodiments, the linear pH gradient is generated using two eluent buffers comprising the same mixture of amines. Typically, the pH of the eluting buffer is dependent on the ratio between Buffer A and B during the elution. In some embodiments, Buffer A has a pH of about 9.1 and Buffer B has a pH of about 3.4, and the concentration of Buffer A decreases from about 40% to about 60% and Buffer B increases from about 60% to about 40%. In some embodiments, Buffer A has a pH of about 9.1 and Buffer B has a pH of about 3.4, and the concentration of Buffer A decreases from about 100% to about 0% and Buffer B increases from about 0% to about 100%. In some embodiments, Buffer A has a pH of about 9.1 and Buffer B has a pH of about 3.4, and the concentration of Buffer A decreases from about 90% to about 0% and Buffer B increases from about 10% to about 100%. In some embodiments, the increment of % Buffer B per minute is in the range of about 0.1% to about 10% or in the range of about 3.5% to about 4.5%. In some embodiments, the increment of % Buffer B per minute is selected from the group consisting of about 3.5%, 3.75%, 4%, 4.25%, or 4.5%. In some embodiments, the increment of % Buffer B per minute is about 3.5%. In some embodiments, the elution conditions comprise a flow rate of about 0.1 to about 1.4 mL/minute, or about 0.25 to 1.0 mL/minute, or 0.5 mL/minute to 0.8 mL/minute, or about 0.8 to about 1.0 mL/minute. In some embodiments, the elution conditions comprise a flow rate of about 1 mL/minute.

In some embodiments, the elution conditions comprise the following steps: from 90% to 100% Buffer B at a linear increase/slope of about 0.1% to about 10%, about 0.5% to about 10%, or about 3.5% to about 4.5% Buffer B per minute.

In some embodiments, the elution conditions comprise the following steps: from 0% to 100% Buffer B at a linear increase/slope of about 0.1% to about 10%, about 0.5% to about 10%, or about 3.5% to about 4.5% Buffer B per minute.

In some embodiments, the elution conditions comprise the following steps: from 90% to 100% Buffer B at a linear increase/slope of about 3.5% Buffer B per minute.

In some embodiments, the elution conditions comprise the following steps: from 0% to 100% Buffer B at a linear increase/slope of about 3.5% Buffer B per minute.

In some embodiments of the methods, the anion exchanger is a weak or a strong anion exchanger. In some embodiments of the method, the anion exchanger consists of quaternary ammonium positively charged groups. In some embodiments of the method, the anion exchanger is based on about 1 to about 1000 µm e.g. 5 µm polymer beads. In some embodiments of the method, the polymer beads consist of poly(styrene/divinyl/benzene). In some embodiments of the method, the anion exchanger consists of non-porous or porous particles e.g. the pores of the particles are in the range of about 120 to 1000 Ångstrom (Å). In some embodiments of the method, the anion exchanger consists of non-porous particles. In some embodiments of the method, the anion exchanger consists of monodisperse particles.

In some embodiments of the method, an anion exchange column having at least one of the following characteristics is used: a width in the range of 1.7 to 10 mm (e.g. 4.6 mm), and a length in the range of 10 to 250 mm (e.g. 250 mm).

In some embodiments of the method, an anion exchange column having a width in the range of 1.7 to 10 mm (e.g. 4.6 mm) and a length in the range of 10 to 250 mm (e.g. 250 mm) is used.

In some embodiments of the methods, the method consists of one step chromatographic method e.g. one type of chromatographic method without additional chromatographic and/or separation step(s).

In some embodiments, the purification method is carried out by an anion exchange High-Performance Liquid Chromatography, a Fast Protein Liquid Chromatography (FPLC) and/or by a stand-alone column with or without a connected detector.

In some embodiments, the method is for analytical purposes.

In certain embodiments, provided herein is a purified α-thrombin obtainable by the methods provided herein.

In another aspect, provided herein is an isolated homogenous post-translationally modified α-thrombin. In some embodiments, the α-thrombin is from a mammalian plasma source e.g. from a human or pig plasma source. In another aspect, provided herein is an isolated homogenous post-translationally modified α-thrombin from mammalian blood or plasma source.

In some embodiments, the post-translationally modification is glycosylation. In some embodiments, the post-translationally modification is glycosylation and sialylation. In some embodiments, the homogenous post-translationally modified α-thrombin is represented by a single/particular glycoform. In some embodiments, the α-thrombin glycoform is further sialylated. In some embodiments, the α-thrombin glycoform is homogenously sialylated. In some embodiments, the isolated homogenous post-translationally modified α-thrombin is homogeneously glycosylated α-thrombin. In some embodiments, the isolated homogenous post-translationally modified α-thrombin is represented by one particular glycoform. In some embodiments, the isolated homogenous post-translationally modified α-thrombin is homogeneously sialylated α-thrombin.

In yet another aspect, provided herein is a formulation comprising a purified α-thrombin or an isolated homogeneous post-translationally modified α-thrombin as disclosed herein. In some embodiments, the purified α-thrombin or an isolated homogeneous post-translationally modified α-thrombin is obtained by the methods disclosed herein. In some embodiments of the formulation, the α-thrombin is from mammalian plasma source. In some embodiments, the α-thrombin is from blood or plasma source. In some embodiments, the formulation comprises a pharmaceutically acceptable carrier or diluent. The formulation disclosed herein can be frozen or lyophilized.

In another aspect, provided herein is a method of providing a hemostatic treatment, sealing, graft fixation, wound healing and/or anastomosis, to a surface in a subject, comprising applying to the surface a formulation comprising the purified α-thrombin, the homogeneous post-translationally modified α-thrombin or the β-thrombin. The formulation can be applied with a solution comprising fibrinogen. The surface can be a bleeding or a non-bleeding site. The subject may be a human subject.

In another aspect, the invention relates to the use of a formulation comprising an isolated homogenous post-translationally modified α-thrombin, a purified α-thrombin or β-thrombin as disclosed hereinabove for hemostatic treatment, sealing, graft fixation, wound healing, anti-adhesion and/or anastomosis.

In another aspect, provided is a kit comprising a container such as an ampoule, a vial and/or a syringe which includes the purified α-thrombin, the homogeneous post-translationally modified α-thrombin or the β-thrombin as disclosed hereinabove; and optionally an application device and/or instructions for use.

In another aspect, provided is a kit comprising a container comprising an isolated homogenous post-translationally modified α-thrombin or a purified homogenous α-thrombin glycoform as disclosed hereinabove as a first component.

In some embodiments, the kit comprises a container comprising gelatin e.g. as a second component. The kit may further include fibrinogen. In some embodiments, the kit comprises a container comprising fibrinogen e.g. as a second component. The kit may include at least one container and at least one label. Suitable containers include, for example, ampoules, vials, syringes and tubes. The containers can be made of, for example, glass, metal or plastic.

These and other aspects and embodiments of the invention will become evident upon reference to the following detailed description of the invention and the figures.

All embodiments disclosed herein relating to purification and/or quantification of α-thrombin also relate to purification and/or quantification of β-thrombin.

In all Figs. the sample depictions is shown from top to bottom based on the beginning of the chromatogram, the sample injected (from top to bottom) is listed on the chromatogram. The runs of the different samples are shown in one figure as stacked overlays. In all graphs the y-axis is labeled as Absorbance Unit (AU); and the x-axis is labeled as minutes.

Figure 2:
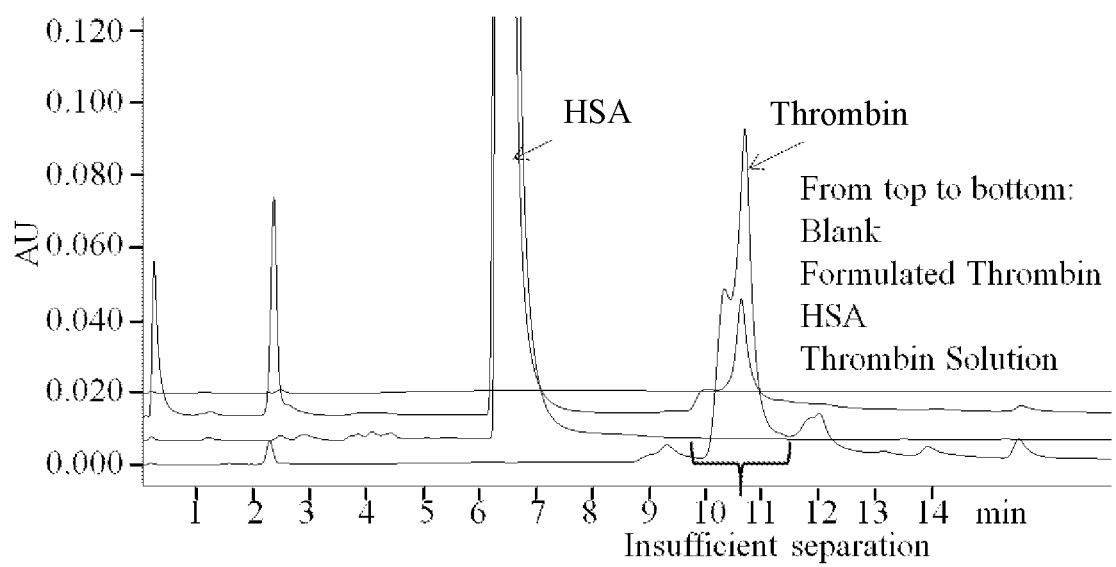

FIG. 2 shows a zoom-in view of a representative chromatogram in the region of the eluting peaks obtained using Anion Exchange High-Performance Liquid Chromatography (AEX-HPLC) and elution with a linear NaCl salt gradient at pH 8.0. The samples injected were: a) 30 µL thrombin solution; b) 100 µL formulated thrombin; c) 100 µL 5 mg/ml HSA; and d) 100 µL Buffer A as a blank sample.

Figure 3:
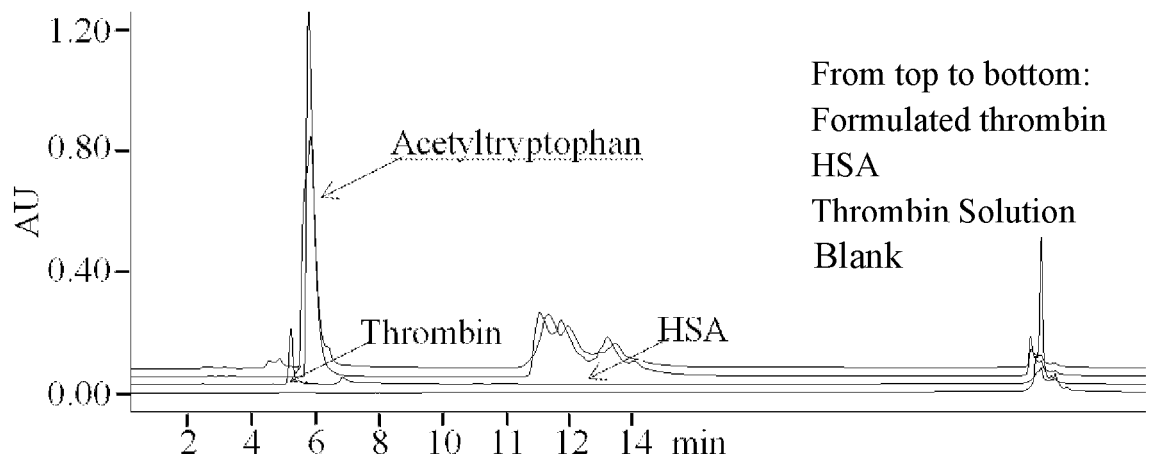

FIG. 3 shows a representative chromatogram obtained for different samples injected into the AEX-HPLC and eluted using a linear NaCl salt gradient at pH 6.0. The samples injected were: a) 30 µL thrombin solution; b) 100 µL formulated thrombin; c) 100 µL 5 mg/ml HSA; and d) 100 µL Buffer A as a blank sample.

Figure 4:
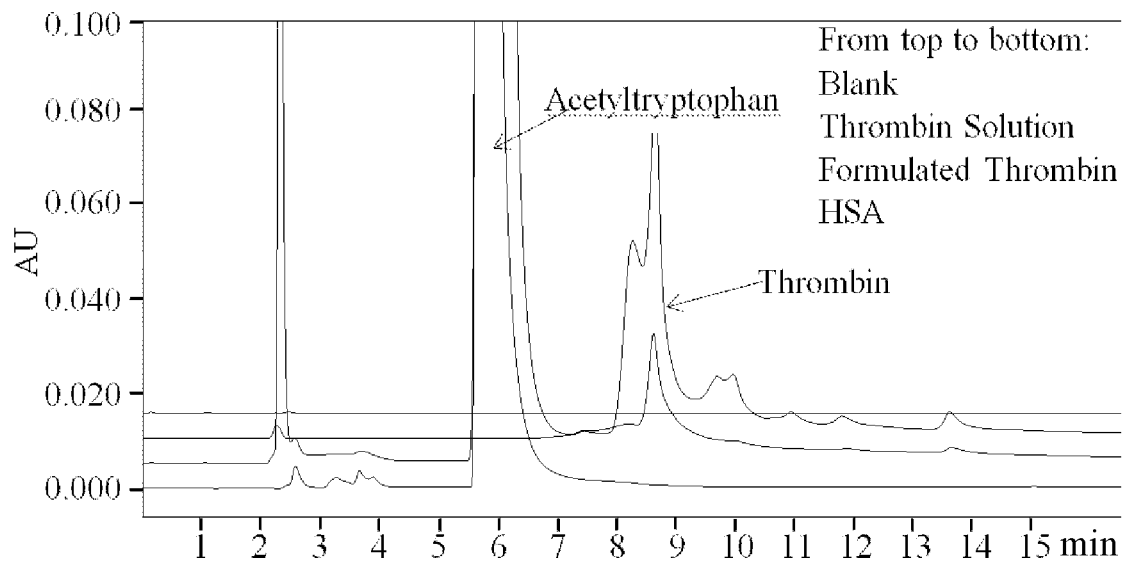

FIG. 4 shows a zoom-in view of a representative chromatogram in the region of the eluting peaks obtained using AEX-HPLC with a linear NaCl salt gradient at pH 7.5. The samples injected were: a) 30 µL thrombin solution; b) 100 µL formulated thrombin; c) 100 µL 5 mg/ml HSA; and d) 100 µL Buffer A as a blank sample.

Figure 5:
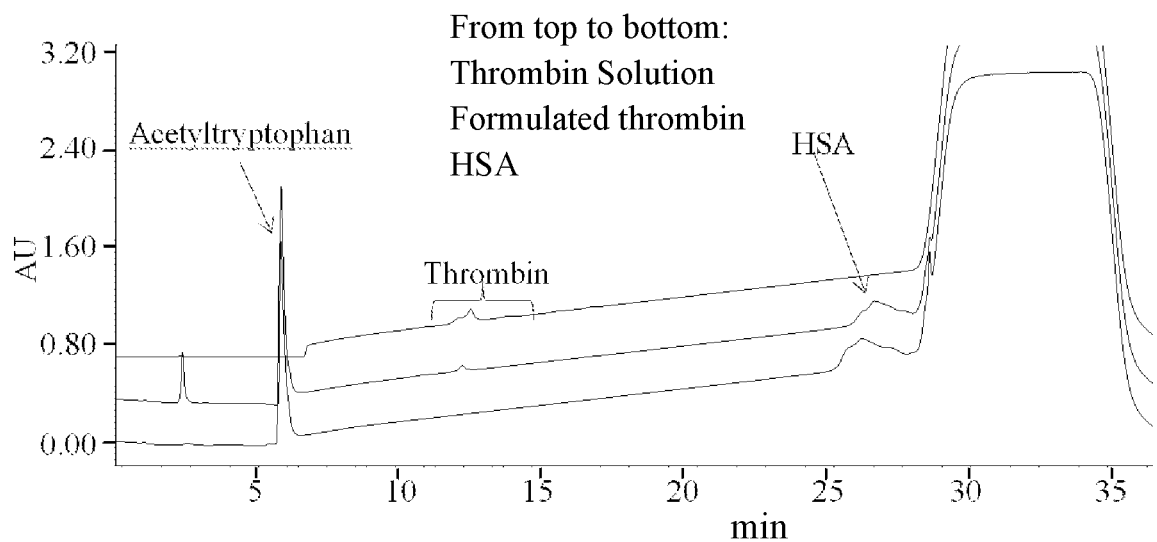

FIG. 5 shows a representative chromatogram in the region of the eluting peaks obtained using AEX-HPLC with a linear $NaNO_3$ salt gradient at pH 8.0. The samples injected were: a) 30 µL thrombin solution; b) 100 µL formulated thrombin; and c) 100 µL 5 mg/ml HSA.

Figure 6:
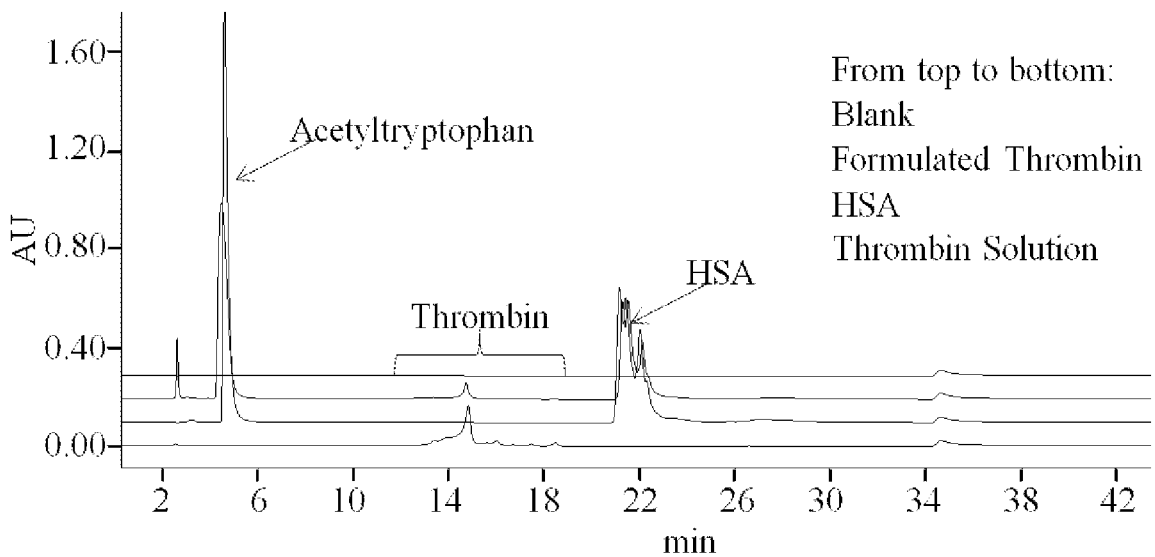

FIG. 6 shows a representative chromatogram of the samples injected obtained using AEX-HPLC with a linear pH gradient between pH 9.1 to pH 3.4. The samples injected were: a) 30 µL thrombin solution; b) 100 µL formulated thrombin; c) 100 µL 5 mg/ml HSA; and d) 100 µL Buffer A as a blank sample. The elution was carried out with amine based buffers.

Figure 7:
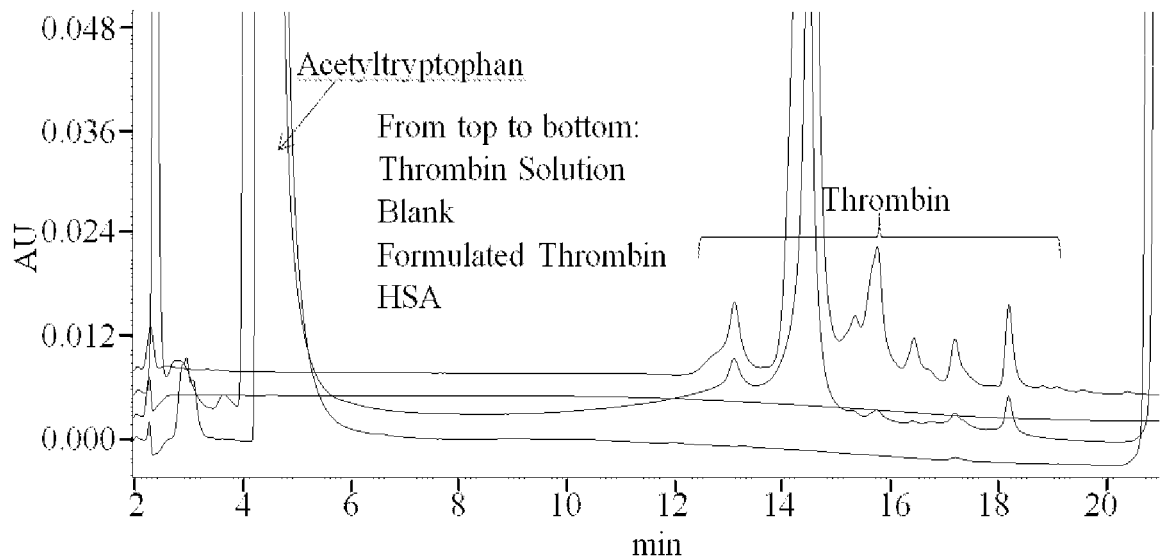

FIG. 7 is a zoom-in view of the thrombin eluting region in the chromatogram shown in FIG. 6.

Figure 8:
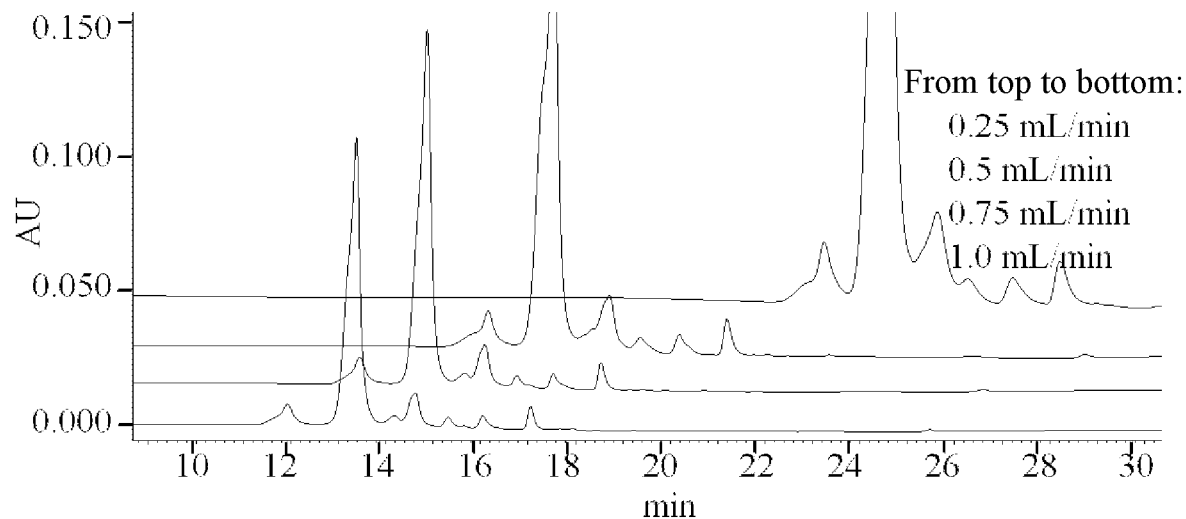

FIG. 8 shows a zoom-in view of the chromatograms obtained using AEX-HPLC and elution at a linear pH gradient at different flow rates: 0.25, 0.5, 0.75, and 1 mL/min. The injected sample was 30 µL thrombin solution for each tested flow rate.

Figure 9:
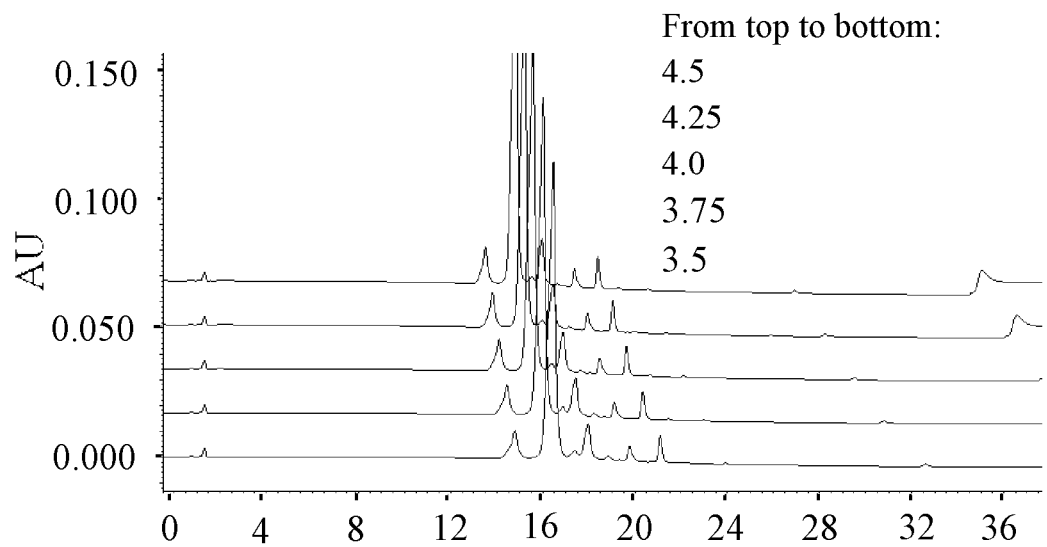

FIG. 9 shows the effect of the linear gradient slope on the separation/resolution (evaluated by visual inspection). Different increments of % Buffer B per minute were evaluated: 4.5%, 4.25%, 4%, 3.75%, and 3.5%. The injected sample was 30 µL thrombin solution for each tested increment.

Figure 10:
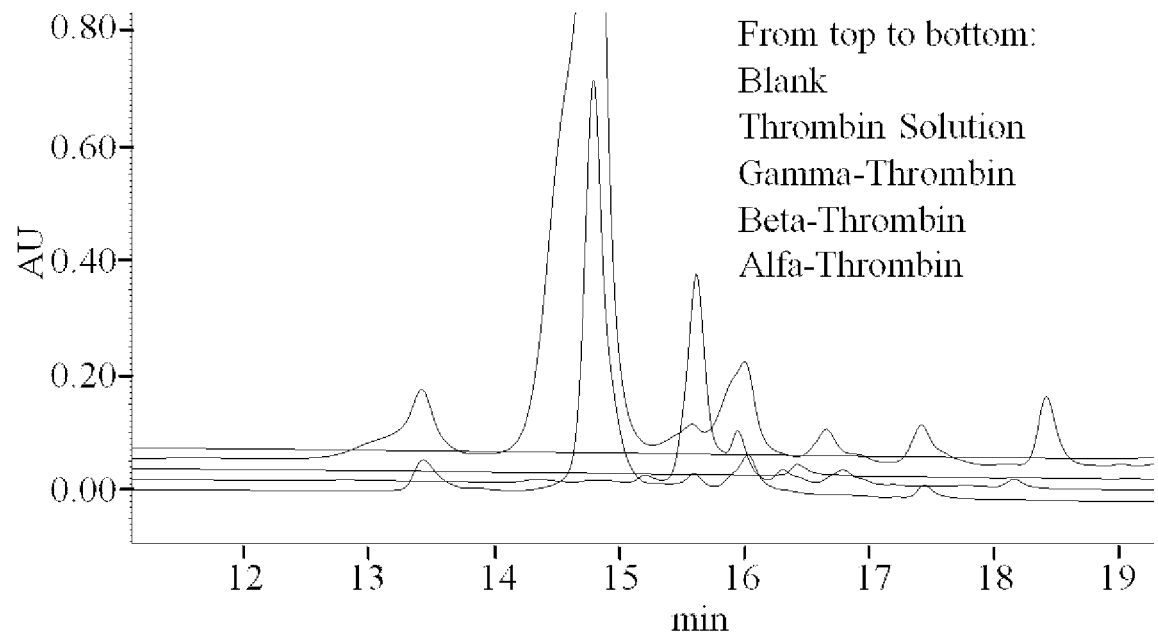

FIG. 10 shows overlaid chromatograms of α, β and γ thrombin standards, thrombin solution and Buffer A as a blank sample obtained using AEX-HPLC at a flow rate of 1.0 mL/min. Different thrombin peaks were identified for the thrombin solution by comparison to the thrombin commercial standards.

Figure 11:
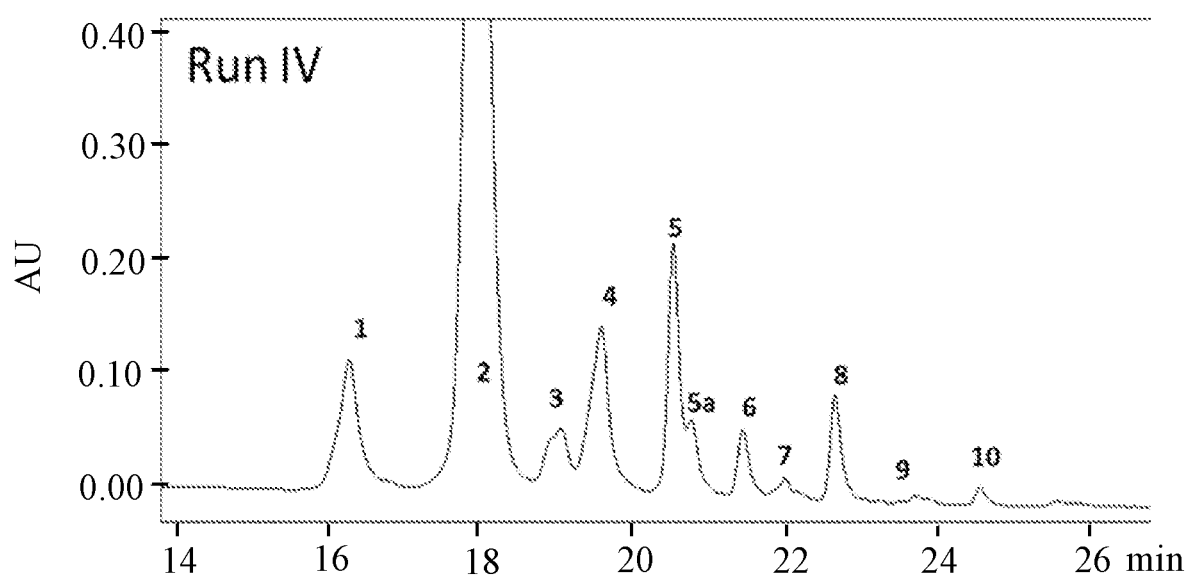

FIG. 11 shows different thrombin peaks separated from a thrombin solution using an AEX-HPLC linear pH gradient between 100% Buffer A to 100% Buffer B in a slope of 3.5% B per minute. The eluted peaks were collected and further identified using Western Blot as a qualitative tool.

Figure 12:
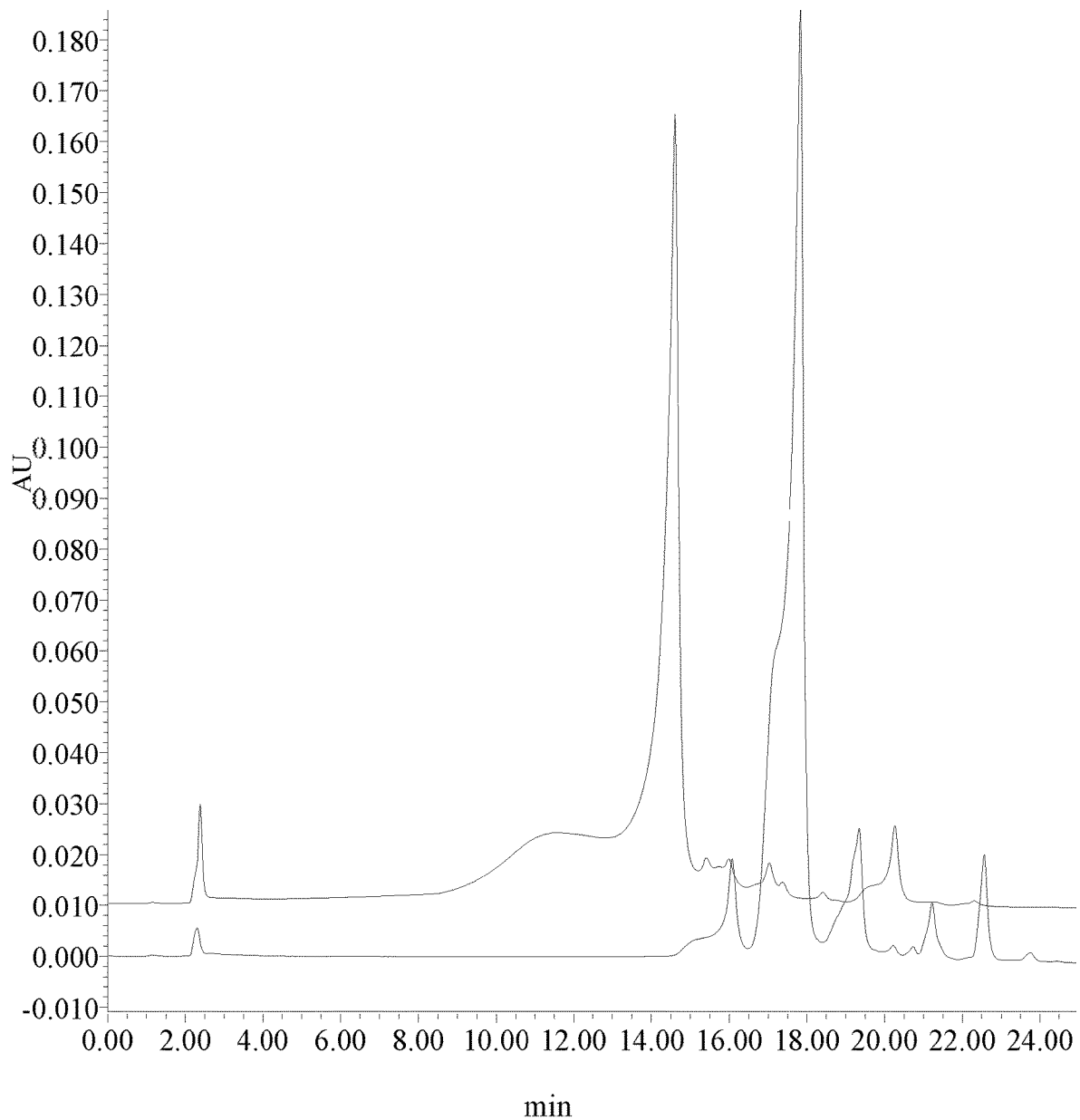

FIG. 12 shows a chromatogram with different thrombin species resolved by HPLC-AEX. A thrombin solution subjected to sialic acid removal and a thrombin solution without treatment were injected. The results show that sialic acid removal affects the charge of the present thrombin species which in turn affects the elution profile resulting in an overall shift of the peaks to the left side of the chromatogram (as compared to an un-treated thrombin solution).

Figure 13:
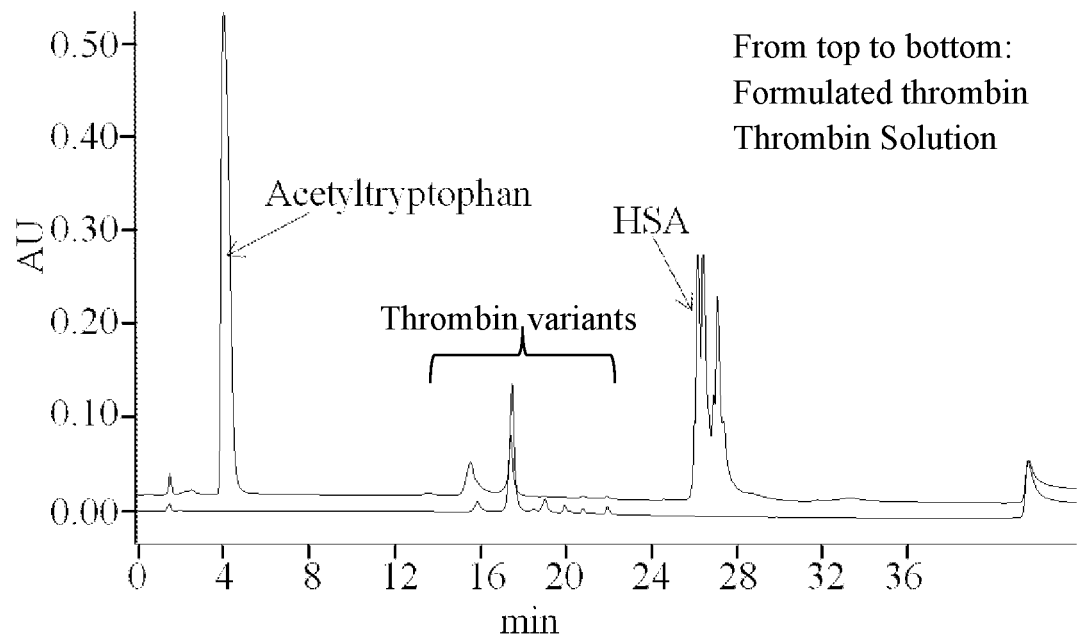

FIG. 13 shows a full length chromatogram of an injected thrombin sample obtained using an AEX-HPLC linear pH gradient, with an increment of 3.5% Buffer B per minute, and flow conditions of 1.0 mL/min. The results show complete separation between human serum albumin, several α-thrombin peaks corresponding to different homogenously post-translationally modified α-thrombin species and acetyl-tryptophan.

Figure 14:
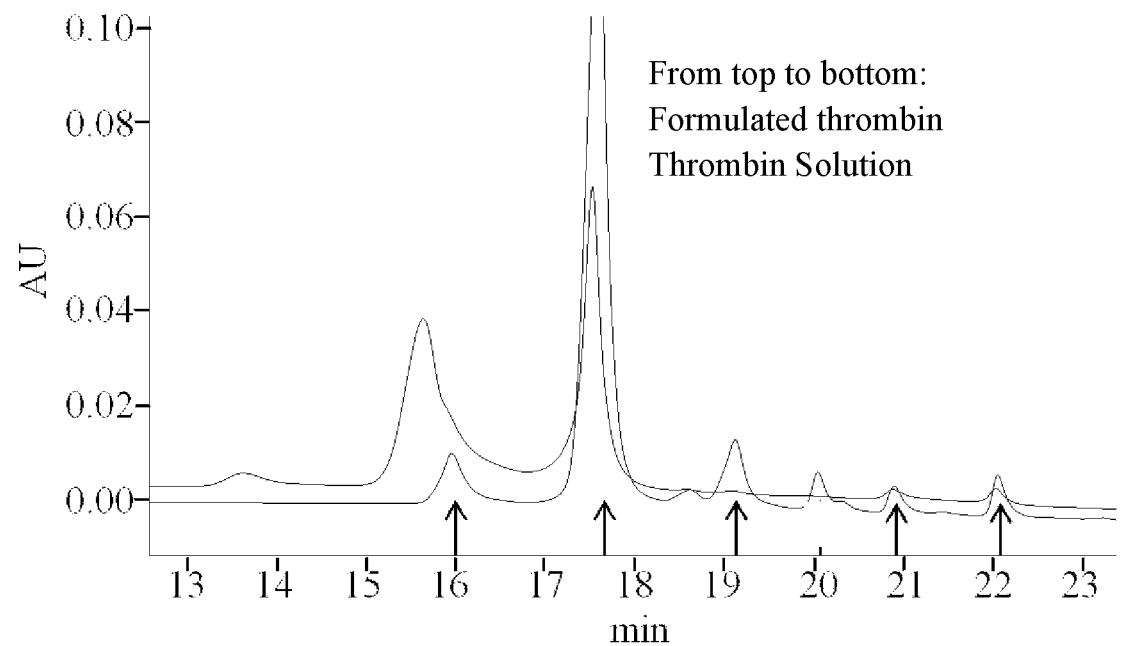

FIG. 14 shows a zoom-in view of the α-thrombin species and degradation polypeptides eluting region.

DETAILED DESCRIPTION OF THE INVENTION

The method provided herein is based, in part, on the discovery that a homogeneous e.g. with respect to the post-translational modification (e.g. glycosylation and/or sialylation level), intact α-thrombin may be isolated/purified from a heterogeneous protein solution by utilizing Anion Exchange Chromatography (AEX). Also, the method according to the invention is based on the discovery that α-thrombin or β-thrombin can be isolated/purified from a solution comprising other proteins e.g. a stabilizer such as human serum albumin and/or bovine serum albumin.

It was surprisingly found that the method according to the invention enables a high resolution purification and/or quantification of α-thrombin or β-thrombin in the presence of high amounts of other proteins relative to thrombin concentration in the solution.

More particularly, the method according to the invention enables to purify and/or quantify different homogenous post-translationally modified α-thrombin species (e.g. homogenous α-thrombin glycoforms) in high resolution from a heterogeneous solution comprising high amounts of other proteins e.g. stabilizers such as human serum albumin, bovine serum albumin and the like.

In some embodiments, the other proteins, e.g. serum albumin, are present in the solution at a concentration of about 0.4 to about 50 mg/ml e.g. about 5 to about 6.5 mg/ml. In some embodiments, the thrombin concentration in the solution is in the range of about 100 to about 10000 IU/ml e.g. about 800 to about 1200 IU/ml or about 0.3 mg/ml. In some embodiments, the ratio of thrombin (IU) to other proteins (mg) is in the range of about 1:10 to about 1:40 or about 1:14 to about 1:27.

In particular, provided herein is a one-step chromatographic method for purification and/or quantification of α-thrombin from a thrombin comprising solution by providing good peak separation of intact, post-translationally modified α-thrombin from its degradation polypeptides, and other proteins in a thrombin formulation. Also, provided herein are tools for separating between α-thrombin, its degradation polypeptides and other proteins (e.g. HSA) in a thrombin solution/formulation.

"Intact α-thrombin" refers, for example, to an undamaged, non-degraded and/or functional form of α-thrombin.

Hitherto, thrombin was purified and analyzed using reverse phase chromatography, hydrophobic interaction chromatography, cation exchange chromatography and/or SDS-PAGE and Western Blot.

Provided herein is a method for purifying α-thrombin from a solution comprising the α-thrombin and at least one of an α-thrombin degradation polypeptide (e.g. β-thrombin and/or γ-thrombin polypeptides) or another protein, the method comprising the steps of: contacting the solution with an anion exchanger; separating the α-thrombin from at least one of the α-thrombin degradation polypeptide or the another protein by an anion exchange chromatography using differential elution conditions e.g. pH gradient; and collecting an α-thrombin fraction, thereby obtaining purified α-thrombin.

Also, provided herein is a method for purifying a homogenous post-translationally modified α-thrombin species (e.g. homogenous α-thrombin glycoform) from a solution comprising heterogeneous post-translationally modified α-thrombin species (e.g. heterogeneous glycosylated α-thrombin species), and optionally at least one of an α-thrombin degradation polypeptide or another protein; the method comprising the steps of: contacting the solution with an anion exchanger; separating the homogenous post-translationally modified α-thrombin species from the other α-thrombin post-translationally modified species; and optionally from the α-thrombin degradation polypeptide and/or the another protein; by differential elution conditions e.g. pH gradient, and collecting a homogenous post-translationally modified α-thrombin fraction, thereby obtaining purified homogenous post-translationally modified α-thrombin species.

The terms "purifying", "to purify" and the like refer to removing, isolating, or separating α-thrombin (e.g. a homogeneous, post-translationally modified α-thrombin) or β-thrombin from a solution comprising it. The α-thrombin containing solution may also comprise α-thrombin degradation polypeptide (β-thrombin and/or γ-thrombin), another protein and/or other α-thrombin post-translationally modified species. The β-thrombin containing solution may also comprise α-thrombin, γ-thrombin, another protein and/or α-thrombin post-translationally modified species.

The term "contacting" refers to any type of a combining action which brings the solution into sufficiently close contact with the anion exchanger comprising the positively charged groups, in a manner that a binding interaction will occur between the positively charged groups and any binding partner, e.g. α-thrombin or β-thrombin, present in the solution. The solution can be incubated with the anion exchanger for a sufficient period of time, e.g. 1 min or more, which allows contacting and/or binding between the positively charged groups and the α-thrombin or β-thrombin.

The term "α-thrombin fraction" typically refers to the fraction collected following elution of the loaded anion exchanger (e.g. loaded column) with a buffer under differential elution conditions. In one embodiment, the collected α-thrombin fraction consists of only α-thrombin. In another embodiment, the collected α-thrombin fraction consists of one homogenous α-thrombin species. In another embodiment, the collected α-thrombin fraction consists of homogenous α-thrombin glycoform fraction.

The term "purified α-thrombin", typically, refers to an α-thrombin preparation obtained following isolation of the α-thrombin from α-thrombin degradation polypeptides and/or another protein present in the starting thrombin comprising solution using an anion exchange chromatography method. The term "purified α-thrombin", as used herein, also refers to a homogeneous post-translationally modified α-thrombin e.g. homogeneously glycosylated and/or sialylated α-thrombin preparation obtained following isolation of the homogeneously post-translationally modified α-thrombin from heterogeneously post-translationally modified α-thrombin solution using an anion exchange chromatography method. The term "purified homogenous α-thrombin glycofrom", typically, refer to a homogenous α-thrombin glycoform preparation obtained following isolation of the α-thrombin glycoform from α-thrombin degradation polypeptides, heterogeneous glycosylated α-thrombin species and/or another protein present in the starting thrombin comprising solution using an anion exchange chromatography method.

In one embodiment, the purified α-thrombin is an intact protein without degradation polypeptides.

In one embodiment, the purified α-thrombin is a homogenous post-translationally modified α-thrombin species. In another embodiment, the purified α-thrombin is an unmodified α-thrombin species. In another embodiment, the purified α-thrombin is a homogenous α-thrombin glycoform.

A purified α-thrombin preparation may consist of a homogenous post-translationally modified species isolated from a solution comprising various post-translationally modified α-thrombin. The starting thrombin solution may also comprise unmodified α-thrombin species.

The isolated post-translationally modified α-thrombin may be glycosylated or glycosylated and sialylated. The glycosylation and/or sialylation degree may vary between the different species. The antenna can be branched at varying degrees from di-antennary to penta-antennary. The sialic acid can be any of the derivatives of the neuraminic acid (5-amino-3,5-dideoxy-D-glycero-D-galacto-non-2-ulosonic acid), like N-acetylneuraminic acid or N-glycolylneuraminic acid.

"α-thrombin" may include unmodified α-thrombin, homogeneous or heterogeneous α-thrombin, homogenous post-translationally modified α-thrombin, for example, homogenously glycosylated α-thrombin or homogenously glycosylated and homogenously sialylated α-thrombin or homogeneously sialylated α-thrombin; and heterogeneously post-translationally modified α-thrombin e.g. heterogeneously glycosylated or glycosylated and sialylated α-thrombin. The α-thrombin may be from a mammalian blood and/or plasma source e.g. human, bovine plasma or pig plasma source or from a recombinant source.

In some embodiments, the "another protein"/"other proteins" is human serum albumin (HSA) or any other protein included in a thrombin formulation e.g. for stabilization of the formulation. The "another protein" is different from α, β and γ-thrombin. The "another protein" may be numerous proteins which can be found in the blood or plasma such as prothrombin, immunoglobulins, HSA and others. The another protein may be a protein fragment. In some embodiments, the another protein is a stabilizer such as human serum albumin and/or bovine serum albumin.

The term "anion exchange chromatography" refers to a separation technique wherein molecules are separated based on their net charge. Anion exchangers are named for their ability to attract or bind anions or negatively charged particles. Anion exchangers are well known in the art (Practical Protein Chromatography edited by Kenney and Fowell Volume 11; Chapter 16, 249-258; Humana Press, 1992). In anion exchangers, the resin is positively charged and a molecule will bind if the buffer pH is higher than the protein's isoelectric point. The term "isoelectric point" refers to the pH wherein a molecule carries no net charge. In a medium with a pH below the isoelectric point, the molecule carries a net positive charge, above it the molecule carries a net negative charge. The terms "anion exchanger" and "anion exchange matrix" are used herein interchangeably.

The terms "support" and "resin" as used herein include a carrier, or any matrix used to attach, immobilize, carry, or stabilize the positively charged groups. Supports are well known in the art as described in Hermanson G T, Mallia A K and Smith P K 1992 "Immobilization Affinity Ligand Techniques" pp. 1-45 Academic Press, Inc. San Diego, USA.

The support for carrying out the method of the invention can be made of any material which is capable of binding a molecule comprising positively charged groups i.e. a molecule comprising chemical groups which carry a positive charge. Solid supports include, but are not limited to, matrices, columns, coverslips, chromatographic materials, filters, microscope slides, test tubes, vials, bottles, ELISA supports, glass or plastic surfaces, chromatographic membranes, sheets, particles, beads, including magnetic beads, gels, powders, fibers, and the like.

In one embodiment of the invention, the support is in the form of a chromatographically utilizable material. In another embodiment of the invention, the support is in the form of a chromatographic membrane. The support can be composed of a hydrophilic material such as agarose, sepharose, acrylic beads, cellulose, controlled pore glass, silica gels, dextranes; hydrophobic material; or an organic artificial/synthetic polymer such as materials based on polyacrylamides or polystyrens. Typical materials/polymers are commercially available under the trade names Sephacryl® (Pharmacia, Sweden), Ultragel® (Biosepara, France) TSK-Gel Toyopearl® (Toso Corp., Japan), HEMA (Alltech Ass. (Deer-field, Ill., USA), Eupergit® (Rohm Pharma, Darmstadt, Germany). Also materials based on azlactones (3M, St. Paul, Minn., USA). In one embodiment, the support is composed of Agarose® or Sepharose®. These materials are commercially available. Typically, anion-exchange resin or anion-exchange polymer is an insoluble matrix (or support structure) normally in the form of small beads, fabricated from an organic polymer substrate.

In some embodiments of the method, the beads are at a size of about 1 to about 1000 μm or e.g. 5 μm. The beads can be non-porous or porous particles. The beads can be monodisperse (i.e. substantially homogenous in size) particles. In one embodiment, the beads used are in the range of 1.7 μm to 10 μm.

The anion exchanger can be a weak or a strong anion exchanger. A weak anion exchanger generally refers to an exchanger which is comprised of a weak base, while a strong anion exchanger generally refers to an exchanger which is comprised of a strong base that is able to sustain its charge over a wider pH range.

In some embodiments of the method, the positively charged groups are selected from the group consisting of ammonium, alkyl ammonium, dialkylammonium, trialkyl ammonium, quaternary ammonium, alkyl groups, $H^+$, $Na^+$, $K^+$, $Ca^+$, $Mg^+$, amino functional group, and a combination thereof.

Resin beads can be suspended in an appropriate medium and the resulting slurry can be used e.g. in a chromatographic column referred to herein as "column purification". Alternatively, the column can be purchased in a pre-packed form.

"Column purification" and "column chromatography" generally refer to a technique in which a solution (the mobile phase) is allowed to travel through a column comprising a packed resin at a certain flow rate, and an individual component or a number of components are adsorbed by the resin (the stationary phase) i.e. by the chromatographic material. The un-bound material can be collected from the other side of the column after the mixture has passed through it. By using certain elution conditions it is possible to alter the bond between the different compounds and the stationary phase, thereby leading to the elution of a specific, purified compound from the column, one at a time. Column purification is well known in the art as described in Practical Protein Chromatography edited by Kenney and Fowell Volume 11; Chapter 16, 249-258; Humana Press, 1992. Typically, a slurry of resin, is poured into the column. After it settles, the column is pre-equilibrated in buffer before the protein mixture/solution is applied. Alternatively, a pre-packed column can be purchased. Unbound proteins appear in the flow-through and/or in subsequent buffer washes. Proteins that bind to the resin are retained and can be eluted by: salt or pH/polarity adjustment. The term "unbound material"/"un-bound fraction" typically refers to the fraction discarded following washing of the loaded column e.g. with the same buffer used for equilibration and/or the buffer used for loading the thrombin containing solution onto the column ("binding buffer"). "A non-isocratic solution" is used as elution conditions. A "non-isocratic solution" typically refers to, e.g. a solution and/or a condition that is different from the solution and/or condition used to load, wash and/or equilibrate the column; and/or to a solution that is different from a solution used in a previous step. Elution conditions employ a shift in the composition of the mobile phase so the factors binding environment created by the binding buffer is changed.

Generally, equilibration is carried out until pH and/or conductivity and/or UV readings are stabilized. In one embodiment, equilibration is carried out with ≥5 column volumes of buffer. In another embodiment, equilibration is carried out with 1 to 5 column volumes of buffer.

The term "elution conditions" refers to the use of a non-isocratic condition e.g. a solution and/or condition different from the solution and/or condition used to load and/or equilibrate the column; and/or different from the solution used in a previous step. The solution and/or conditions used at the starting point and/or at the end point of the elution step (e.g. the gradient elution) may be identical to the solution and/or conditions used during the washing, loading, and/or regeneration steps. The term "elution conditions" may also refer to a gradient elution during which salt concentration and/or changes in pH/polarity occurs. The elution conditions are such that the proteins and degradation polypeptides are separated and eluted differentially. The method according to the invention comprises at least one elution step with a non-isocratic solution. Elution conditions, typically involve an increase in salt concentration and/or changes in pH/polarity. It was found herein that using a pH gradient for elution is efficient.

In some embodiments of the methods, the method consists of one chromatography step i.e. a single chromatography step.

Typically, the term "one-step chromatographic method" or "one chromatography step" or "one-step anion exchange chromatography" refers to a method enabling the purification and/or quantitation of the α-thrombin; homogeneous or heterogeneous α-thrombin; homogenously post-translationally modified α-thrombin, for example, homogenously glycosylated α-thrombin or homogenously glycosylated and homogenously sialylated α-thrombin; unmodified α-thrombin; heterogeneously post-translationally modified α-thrombin e.g. heterogeneously glycosylated or glycosylated and sialylated α-thrombin and/or thrombin degradation polypeptides; or β-thrombin that is carried out by the anion exchanger directly on a sample material without additional chromatographic and/or separation step(s).

In one embodiment of the invention, column purification is utilized. In another embodiment, an Anion Exchange High-Performance Liquid Chromatography method is used. The column may be regenerated after elution of the solution ingredients for repetitive use. The total run time from loading to regeneration can be in the range of 30 to 120 minutes e.g. about 46, 55 minutes. In one embodiment, the gradient separation takes 28.6 minutes.

Separation according to the invention is carried out by employing differential elution conditions. The term "differential elution conditions" refers to conditions that allow separation of α-thrombin from its degradation polypeptides and/or from another protein; separation of a homogenous post-translationally modified α-thrombin species from thrombin degradation polypeptides, another protein and/or heterogeneous post-translationally modified α-thrombin species; separation of a homogenous α-thrombin glycoform from heterogeneous post-translationally modified α-thrombin species e.g. glycosylated α-thrombin species; separation of a homogenous α-thrombin glycoform from at least one of α-thrombin degradation polypeptides, another protein or heterogeneous post-translationally modified α-thrombin species; and/or separation of β-thrombin from α-thrombin, γ-thrombin and/or another protein.

The elution conditions may involve alterations in the salt concentration and/or in the pH of the elution buffer. In one embodiment, the differential elution conditions comprise alterations in the pH e.g. a pH gradient. In one embodiment, the resins used according to the invention are adequate to work at a pH range according to the invention. In one embodiment, the resins are suitable to be subjected to organic materials (such as methanol and/or acetonitrile).

The column volume can be in the range of about 0.03 to about 53 mL. In one embodiment of the invention, the column volume is about 4.1 mL e.g. 4.15 mL. In another embodiment, most of the peaks are collected within one column volume.

In an additional embodiment, the method is an analytical method, e.g. physico-chemical analytical method, and can be carried out as a one-step chromatographic method.

In some embodiments, the method further includes identifying the separated α-thrombin, β-thrombin and/or γ-thrombin containing fractions.

In some embodiments, the method further includes identifying the different post-translationally modified α-thrombin. The different glycosylations can be analyzed using Mass Spectroscopy, capillary electrophoresis, by using different HPLC methods or by any other methods known in the art.

In one embodiment, the different fractions/peaks are visually identified after injecting the sample set. Typically, the peaks profile is robust and therefore each peak can be easily identified. In another embodiment, the different thrombin peaks are identified by injecting into the HPLC α, β and γ thrombin standards, and identifying the correlating peaks of the thrombin solution. In another embodiment, the different thrombin peaks are identified by Western Blot analysis by running the eluted peaks against α, β and γ thrombin standards and/or based on the known molecular size of α-, ρ- and γ-thrombin. Provided herein is a one-step chromatographic method for quantifying α-thrombin in a solution comprising the α-thrombin and at least one of an α-thrombin degradation polypeptide or another protein, the method comprising the steps of: separating the α-thrombin from the at least one of the α-thrombin degradation polypeptide or the another protein on anion exchange chromatography by differential elution conditions; collecting an α-thrombin fraction; and quantifying the α-thrombin.

Provided herein is a one-step chromatographic method for quantifying a homogenous post-translationally modified α-thrombin (e.g. homogenous glycoform) in a solution comprising heterogeneous post-translationally modified α-thrombin and optionally at least one of an α-thrombin degradation polypeptide or another protein, the method comprising the steps of: separating the homogenous post-translationally modified α-thrombin from the solution on anion exchange chromatography by differential elution conditions; collecting the homogenous post-translationally modified α-thrombin fraction; and quantifying the homogenous post-translationally modified α-thrombin.

Provided herein is a one-step chromatographic method for quantifying α-thrombin in a solution comprising the α-thrombin and at least one of an α-thrombin degradation polypeptide or another protein, the method comprising the steps of: contacting the solution with an anion exchanger; separating the α-thrombin from the at least one of the α-thrombin degradation polypeptide and/or the another protein on anion exchange chromatography by differential elution conditions; and quantifying the α-thrombin.

In some embodiment, the method comprises separating the α-thrombin from the at least one of the α-thrombin degradation polypeptide and the another protein on anion exchange chromatography by differential elution conditions.

In some embodiments, the method further includes quantifying one or more degradation polypeptides e.g. β-thrombin and/or γ-thrombin polypeptides.

Also, provided herein is a one-step chromatographic method for quantifying homogenous post-translationally modified α-thrombin in a solution comprising heterogeneous post-translationally modified α-thrombin; and optionally at least one of an α-thrombin degradation polypeptide or another protein, the method comprising the steps of:

contacting the solution with an anion exchanger; separating the homogenous post-translationally modified α-thrombin from the heterogeneous post-translationally modified α-thrombin; and optionally from the at least one of the α-thrombin degradation polypeptide and/or the another protein; on anion exchange chromatography by differential elution conditions; and quantifying the homogenous post-translationally modified α-thrombin. In one embodiment, the solution comprises at least one of α-thrombin degradation polypeptide (β-thrombin and/or γ-thrombin); and/or another protein.

In some embodiments, the solution further comprises at least one of an α-thrombin degradation polypeptide or another protein, and the method includes separating the homogenous post-translationally modified α-thrombin also from the at least one of the α-thrombin degradation polypeptide and/or the another protein. In some embodiments, the method includes separating the homogenous post-translationally modified α-thrombin from the at least one of the α-thrombin degradation polypeptide and the another protein.

Quantification can be carried out, for example, by calculating the integration e.g. by measuring the area under the peak of a chromatogram. The peaks can be quantitated either by integration of the peak and comparing the peak area to the total area eluted or by evaluating the peak height. The area or height can be translated into absolute numbers if a standard is used or the relative peak area can be evaluated.

In some embodiments of the methods, the separating step includes applying differential elution conditions. In some embodiments the elution conditions include applying a pH gradient. In some embodiments the elution conditions include applying a linear pH gradient. Typically, a linear pH gradient is defined as a gradient which gradually and equally changes the pH over time. In some embodiments, the pH gradient is from about pH 9.1 to about pH 3.4. In some embodiments the linear pH gradient is generated using an eluent comprising an amine or a mixture of amines. In some embodiments, the eluent comprises a mixture of amines. In some embodiments, the amine based buffer comprises piperazine, triethanolamine, bis-tris propane, 1-methylpiperazine and a mixture thereof. In some embodiments, the concentration of each amine in the buffer is in the range of about 1 to about 100 mM e.g. in the range of about 10 to about 20 mM or about 20 mM. Buffers with similar characteristics, suitable for the creation of a pH gradient, can be used e.g. phosphate buffers at different pH values. Alternative compounds, not listed herein can be used to build a buffer system suitable for the elution of thrombin from an anion exchanger.

The results show that AEX-HPLC and elution using a linear gradient between pH 9.1 to pH 3.4 lead to good resolution between HSA, acetyltryptophan, α-thrombin degradation polypeptides and α-thrombin. Accordingly, in one embodiment, a linear pH gradient elution step between pH 9.1 to pH 3.4 is used as differential elution conditions. In one embodiment, the HPLC comprises a loading step of 5 minutes, at a flow rate of 0.80 mL/min; a linear pH gradient elution step of 20 minutes, at a flow rate of 0.80 mL/min, the linear pH gradient is generated by using two eluent buffers comprising the same mixture of amines, the concentration of Buffer A decreases from 90% to 0% and Buffer B increases from 10% to 100%, the increment of Buffer B is 4.5% per minute. In another embodiment, the HPLC comprises a column equilibration step of 15 minutes, at a flow rate of 0.80 mL/min. In another embodiment, the HPLC comprises a column regeneration step of 5 minutes, at a flow rate of 0.80 mL/min.

In some embodiments, the temperature during the elution step is in the range of about 10° C. to about 50° C. e.g. about 25° C.

In some embodiments, the flow rate during the linear pH gradient elution step is 0.25, 0.5, 0.75, and 1 mL/min. The results show that the resolution between α-thrombin and its degradation polypeptides increases with increasing flow rates and that the best resolution was achieved at a flow rate of 1.0 mL/min. Accordingly, in one embodiment, the flow rate during the linear pH gradient elution step is higher than 0.75 mL/min e.g. about 1.0 mL/min.

The results show that eluting the proteins from the column with a wider pH range leads to a better separation between the peaks. Accordingly, in one embodiment, a linear pH gradient elution step is generated by using two eluent buffers comprising the same mixture and concentrations of amines, the gradient concentration of Buffer A decreases from 100% to 0% and Buffer B increases from 0% to 100%, the increment of Buffer B is about 4.5% per minute. In such an embodiment, the linear pH gradient elution step can be about 22 minutes.

The total run time from loading the thrombin solution onto the column and up to column regeneration step (e.g. including a loading steps, a linear gradient elution step, a column regeneration step and a column equilibration step) can be in the range of 30 to 120 minutes e.g. in the range of 46 to 61 minutes such as about 46, 51, 56, and 61 minutes total run time, and the elution step can be in the range of 20 to 35 minutes e.g. about 20, 25, 30 and 35 minutes. The results show that at 56 and 61 minutes total run times (a gradient elution step length of 30 and 35 minutes), an additional peak eluting in a region distinct to the thrombin peaks was separated as compared to the shorter run times. Accordingly, in one embodiment, a linear gradient elution step of higher than 25 minutes is carried out.

The results show that elution with a linear pH slope gradient of 4.5%, 4.25%, 4%, 3.75%, and 3.5% per minute was efficacious in separation of the different thrombin peaks with an increment of 3.5% having the best separation profile. The slope gradient can be impacted by the increment of the percentage of Buffer B per minute when more than one buffer is used as an eluent buffer. Typically, a lower increase of the percentage of Buffer B per minute results in a shallower slope as compared to a higher increase of the percentage of Buffer B per minute, thereby affecting the elution profile of the proteins. Accordingly, in some embodiments, the elution is carried out at a linear pH gradient between 100% Buffer A to 100% Buffer B with a slope of 3.5-4.5% Buffer B per minute e.g. at a slope of 3.5%.

In some embodiments, the starting solution (to be purified and/or quantified) comprising the α-thrombin further comprises another protein, and substantially lacks degradation polypeptides (e.g. the solution contains less than 10% w/w β-thrombin and/or γ-thrombin relative to the total thrombin amount).

In some embodiments, the starting solution comprising the α-thrombin further comprises degradation polypeptides e.g. β-thrombin and/or γ-thrombin. In some embodiments, the starting solution comprising the α-thrombin further comprises degradation polypeptides without the another protein.

In some embodiments, the starting solution comprising the α-thrombin further comprises degradation polypeptides (e.g. β-thrombin and/or γ-thrombin), and another protein.

In some embodiments, the starting solution comprising the β-thrombin further comprises α-thrombin and lacks γ-thrombin and/or another protein. In some embodiments, the starting solution comprising the β-thrombin further comprises γ-thrombin and lacks α-thrombin and/or another protein. In some embodiments, the starting solution comprising the β-thrombin further comprises another protein and lacks α-thrombin and/or γ-thrombin. In some embodiments, the starting solution comprising the β-thrombin further comprises α-thrombin, and γ-thrombin and lacks another protein. In some embodiments, the starting solution comprising the β-thrombin further comprises α-thrombin, and another protein and lacks γ-thrombin. In some embodiments, the starting solution comprising the β-thrombin further comprises γ-thrombin and another protein and lacks α-thrombin. In some embodiments, the starting solution comprising the β-thrombin further comprises α-thrombin, γ-thrombin and another protein.

The starting solution may comprise heterogeneous post-translationally modified α-thrombin and/or un-modified α-thrombin. In some embodiments, the starting solution comprises another protein. In some embodiments, the starting solution lacks another protein.

The thrombin concentration in the solution may be in the range of from about 2 to about 10000 IU/mL, from about 100 to about 10000 IU/mL, from about 2 to about 4000 IU/mL, about 800 to about 3000 IU/mL or about 800 to about 1200 IU/mL and the total protein concentration may be in the range of about 0.3 to about 55 mg/ml, about 0.3 to about 10 mg/ml or about 1 to about 7 mg/ml. In some embodiments, 1000 IU/ml equals 0.3 mg/ml.

The solution may be at a pH in the range of about 6.9 to about 7.1, and may comprise between 5.0 to 6.5 mg/mL human serum albumin (HSA) and/or other stabilizers such as acetyltryptophan.

A solution comprising α-thrombin may be a solution comprising a thrombin formulation or formulated thrombin (e.g. a thrombin solution comprising excipients and/or stabilizers) e.g. a drug product, e.g. with a thrombin activity in the range of 800-1200 IU/ml, a total protein concentration of about 5.7-6.5 mg/ml, and 5.0 to 6.5 mg/ml human serum albumin (HSA) at pH 6.9-7.1. The thrombin formulation may include other stabilizers e.g. acetyltryptophan. In one embodiment, the HSA used for the formulation of thrombin includes a stabilizer, acetyltryptophan.

As used herein the terms "excipient" refers to an inert substance which is added to the pharmaceutical composition. Examples of excipients include, but are not limited to, human albumin, mannitol, sodium acetate and water for injection. The human albumin in the solution can be in the range of from about 2 to about 8 mg/ml. Mannitol can be in the concentration range of from about 15 to about 25 mg/ml. Sodium acetate can be also added in the solution in the range of from about 2 to about 3 mg/ml.

In one embodiment, the thrombin solution comprises about 3000 IU/ml thrombin, a total protein concentration of about 1 mg/ml, 20 mM sodium acetate at pH 6.9-7.1. In another embodiment, the thrombin formulation comprises thrombin in the range of 800-1200 IU/ml, a total protein concentration of about 5.7-6.5 mg/ml, and 5.0 to 6.5 mg/ml human serum albumin (HSA) at pH 6.9-7.1.

The solution may comprise calcium chloride. Calcium chloride concentration in the solution can be in the range of from about 2 to about 6.2 mg/ml, or in the range of from about 5.6 to about 6.2 mg/ml, such as in the concentration of 5.88 mg/ml.

Thrombin clotting activity can be measured directly, for example, by European Pharmacopeia Assay (0903/1997) procedure, by measuring migration length on a slanted surface (or drop test model), and/or by any other method known in the art.

Thrombin activity may be determined using a coagulation analyzer with a mechanical endpoint detection system to detect clot formation, such as the Diagnostica Stago ST4 Coagulation Analyzer, or a device that measures changes in turbidity due to fibrin clot formation.

Another method by which thrombin activity can be measured is using a chromogenic or fluorogenic peptide substrate for thrombin. Oftentimes, in this method, solubilized thrombin is combined with an excess of chromogenic or fluorogenic substrate. Thrombin will cleave the substrate releasing a chromophore or fluorophore which can be monitored in a spectrophotometer or fluorimeter. Examples of chromogenic or fluorogenic substrates include, β-Ala-Gly-Arg-p-nitroanilide diacetate and Z-Gly-Pro-Arg-AMC [Z=Benzyloxycarbonyl; AMC=7-amino-4-methylcoumarin], respectively. The rate of released chromophore or fluorophore can be correlated to the activity of thrombin.

Thrombin can be prepared from a blood composition. The blood composition can be whole blood or blood fractions, i.e. a fraction of whole blood such as plasma. The origin of the thrombin can be autologous whereby it would be manufactured from the patient's own blood, from pooled blood or fractions. The thrombin solution can be prepared from plasma of human beings or mammals. In one embodiment, the thrombin is prepared by recombinant methods in prokaryotic cells.

In one embodiment, the thrombin solution can be formulated as a sterile solution, pH 6.8-7.2, which contains highly purified human thrombin. The thrombin formulation can contain: human thrombin (800-1200 IU/mL), calcium chloride, human albumin, mannitol, sodium acetate and water for injection. In one embodiment, thrombin is manufactured by chromatographic purification of prothrombin from cryo-poor plasma followed by activation with calcium chloride e.g. as described in U.S. Pat. No. 5,143,838, which is incorporated herein by reference.

In another aspect, provided herein is a one-step analytical method for quantifying α-thrombin in formulated thrombin (e.g. a drug product) including the α-thrombin and another protein (e.g. human serum albumin), the method comprising the steps of: contacting the formulated thrombin with an anion exchanger; separating the α-thrombin from the another protein on anion exchange chromatography by differential elution conditions; and quantifying the α-thrombin. In some embodiments, the differential elution conditions comprise a pH gradient e.g. generated by using an eluent comprising of an amine or a mixture of amines. In some embodiments, an anion exchange High-Performance Liquid Chromatography method is used. In some embodiments, the anion exchanger is made of non-porous particles. In some embodiments, the formulated thrombin further comprises undesired α-thrombin degradation polypeptides (β-thrombin and/or γ-thrombin polypeptides), and the method includes separating the α-thrombin from the degradation polypeptides. In some embodiments, the formulated thrombin does not contain degradation polypeptides.

As used herein, the indefinite articles "a" and "an" mean "at least one" or "one or more" unless the context clearly dictates otherwise.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate ±10%.

"Thrombin" or "thrombin polypeptide" is a mammalian serine protease which is part of the blood coagulation cascade and converts fibrinogen into insoluble strands of fibrin, as well as catalyzing other coagulation-related reactions. In humans, prothrombin is encoded by the F2 gene, and the resulting polypeptide is proteolytically cleaved in the coagulation cascade by Factor Xa with a co-factor (FVa) or other serine proteases to generate thrombin. Thrombin serves, inter alia, as an active component in several hemostasis products. For example, fibrin sealants typically comprise a fibrinogen component and a thrombin component. When both components are mixed (e.g. when applied to a bleeding wound) thrombin cleaves fibrinogen and a fibrin polymer is formed which has hemostatic characteristics. Fibrin sealant is typically a blood product obtained from either commercial sources or some regional blood transfusion centers. Components that are commonly used in the preparation of fibrin glues are fibrinogen, thrombin, Factor VIII, Factor XIII, fibronectin, vitronectin and von Willebrand factor (vWF). Fibrin sealant is typically formed by an enzymatic reaction involving inter alia, fibrinogen, thrombin and Factor XIII. The terms "fibrin sealant" and "fibrin glue" are interchangeable.

Human thrombin is a 295 amino acid protein composed of two polypeptide chains, A and B, joined by a disulfide bond. The B chain of α-thrombin is responsible for thrombin's proteolytic activity on fibrinogen and other proteins and for its autolytic activity leading to the β-thrombin and γ-thrombin degradation polypeptides. Cleavage of the B-chain at the Arg106-Tyr107 bond yields a 70 amino acid B1 fragment and the 188 amino acid β-thrombin (B2) form. The γ-thrombin is generated by further cleavage of the β-thrombin B2-chain at the Lys190-Gly191 bond. Typically, these proteolyzed forms of thrombin have reduced ability to covert fibrinogen into insoluble strands of fibrin than intact α-thrombin.

The human α-thrombin B chain is further post-translationally modified e.g. by glycosylation, possibly resulting in a more potent and/or stable form of thrombin as compared to an unmodified form and/or as compared to other form of post-translational modification (as indicated by Ricardo J. Sola and Kai Griebenow. "Glycosylation of Therapeutic Proteins: An Effective Strategy to Optimize Efficacy". BioDrugs. 2010; 24(1): 9-21 for other glycosylated proteins). Mature α-thrombin has a single N-linked glycosylation site on its "heavy chain". Sialic acid, also referred to as neuraminic acid, is critical to glycoprotein bioavailability, function, stability, and metabolism. The glycosylated form of α-thrombin (in mature, natural human α-thrombin, amino acid residue N416) may be further sialylated with from 1 to 5 sialic acid residues. Accordingly, α-thrombin may contain different sialylation degrees/levels e.g. α-thrombin may vary in the amount of N-acetylneuraminic acid (NANA) residues (sialic acid) in the glycosylation site. The degree of sialylation may influence protein potency and stability. Typically, the higher the sialylation level, the higher the potency and the higher the stability.

The results show that separating α-thrombin by anion exchange chromatography enables the separation of numerous α-thrombin peaks containing different amounts of NANA. The results show that treatment of thrombin with N-acetylneuraminidase, an enzyme capable of removing the NANA residues from the terminal end of glycans, affects the elution profile of thrombin resulting in an overall shift of the peaks to the left side of the chromatogram (as compared to an un-treated thrombin). Accordingly, the method of the invention can be used to purify and/or quantify different α-thrombin glycoforms e.g. having differences in NANA content. In one embodiment, the method according to the invention can be used to purify/isolate different homogenous α-thrombin species containing a substantially identical profile of NANA using AEX-HPLC. In another embodiment, the method according to the invention can be used to purify/isolate homogenously post-translational modified α-thrombin from a proteinatious solution and/or from a solution comprising heterogeneously post-translational modified α-thrombin.

"Post-translational modification" is a step in protein biosynthesis. Proteins are created by ribosomes translating mRNA into polypeptide chains. The polypeptide chains undergo post-translational modifications, e.g. cutting, folding, and other processes, before they mature into the final protein product.

After translation, the post-translational modification of amino acids extends the range of functions of the protein by attaching it to other biochemical functional groups, changing the chemical nature of an amino acid, or making structural changes (e.g. formation of disulfide bridges). Modifications can be glycosylation, phosphorylation, ubiquitination, methylation, nitrosylation, acetylation, lipidation. Typically, modifications control the behavior of a protein e.g. activating or inactivating an enzyme.

Typically, glycosylation has a significant effect on protein folding, conformation, distribution, stability and activity. Glycosylation includes addition of a sugar-moiety to proteins that ranges from simple monosaccharide modifications of nuclear transcription factors to highly complex branched polysaccharide changes. Phosphorylation plays a critical role in the regulation of many cellular processes including cell cycle, growth, apoptosis and signal transduction pathways. Methylation, the transfer of one-carbon methyl groups to nitrogen or oxygen (N- and O-methylation, respectively) to amino acid side chains increases the hydrophobicity of a protein and can neutralize a negative amino acid charge when bound to carboxylic acids. Ubiquitination, ubiquitin is an 8-kDa polypeptide consisting of 76 amino acids that is appended to the Iμ-NH2 of lysine in a target protein via the C-terminal glycine of ubiquitin. Polyubiquitinated proteins are recognized by the 26S proteasome that catalyzes the degradation of the ubiquitinated protein and the recycling of ubiquitin. Methylation is a well-known mechanism of epigenetic regulation, as histone methylation and demethylation influences the availability of DNA for transcription. Amino acid residues can be conjugated to a single methyl group or multiple methyl groups to increase the effects of modification.

An "unmodified α-thrombin" refers to α-thrombin that did not undergo post-translational modifications e.g. non-glycosylated and/or therefore non-sialylated α-thrombin.

A "homogeneous, post-translationally modified α-thrombin" refers to a substantially identical form of α-thrombin e.g. with regards of the glycosylation and/or the sialylation level. The homogeneity between the different α-thrombin molecules is expressed by having the same post-translationally modification, e.g. same glycosylation, however each thrombin molecule can possess different levels and/or forms of other modifications. The α-thrombin can be a glycosylated and/or sialylated form of α-thrombin. In one embodiment, the homogeneous α-thrombin is homogeneously glycosylated. In another embodiment, the homogeneous α-thrombin is homogeneously sialylated. The glycosylated α-thrombin can have from 0 to 5 sialic acid residues. In some embodiments, the homogeneous post-translationally modified α-thrombin is a sialylated α-thrombin having 1, 2, 3, 4 or 5 sialic acid residues.

As used herein, the different/heterogeneous post-translationally modified α-thrombin populations of α-thrombin and unmodified α-thrombin is also known as "different α-thrombin species". The heterogeneous post-translationally modified α-thrombin may possess different glycosylation and/or sialylation forms.

As used herein, an "α-thrombin glycoform" refers to a homogenously glycosylated and/or sialylated α-thrombin species.

In some embodiments, the α-thrombin that is prepared using the method described herein is homogeneous to a level of at least 50%, at least 60%, at least 70%, at least 75%, at least 80%, at least 85%, 90%, at least 91%, at least 92%, at least 93%, at least 94%, at least 95%, at least 96%, at least 97%, at least 98%, at least 99% or at least 100% identity. E.g. 50, 55, 60, 65, 70, 75, 80, 85, 90, 95, 99 or less than 100%, including any range between the disclosed percentages such as 50-55%, 50-60%, 50-65%, 50-70%, 50-75%, 50-80%, 50-85%, 50-90%, 50-95%, 50-99%, 50-100%, 55-60%, 55-65%, 55-70%, 55-75%, 55-80%, 55-85%, 55-90%, 55-95%, 55-99%, 55-100%, 60-65%, 60-70%, 60-75%, 60-80%, 60-85%, 60-90%, 60-95%, 60-99%, 60-100%, 65-70%, 65-75%, 65-80%, 65-85%, 65-90%, 65-95%, 65-99%, 65-100%, 70-75%, 70-80%, 70-85%, 70-90%, 70-95%, 70-99%, 70-100%, 75-80%, 75-85%, 75-90%, 75-95%, 75-99%, 75-100%, 80-85%, 80-90%, 80-95%, 80-99%, 80-100%, 85-90%, 85-95%, 85-99%, 85-100%, 90-95%, 90-99%, 90-100%, 95-99%, 95-100% identity.

The present disclosure provides a method of isolating a homogeneous population/species of α-thrombin e.g. a homogenously post-translationally modified α-thrombin. Furthermore, provided is a purified homogeneous population of α-thrombin and a formulation comprising the isolated homogenous post-translationally modified α-thrombin; and a pharmaceutically acceptable carrier or diluent.

In yet another aspect, provided herein is a formulation comprising purified α-thrombin or an isolated homogeneous post-translationally modified α-thrombin as disclosed herein. In some embodiments, the purified α-thrombin or the isolated homogeneous post-translationally modified α-thrombin is obtained by the methods disclosed herein. In some embodiments, the purified α-thrombin or the isolated homogeneous post-translationally modified α-thrombin is obtainable by the methods disclosed herein. In some embodiments of the formulation, the α-thrombin is from mammalian plasma source. In some embodiments, the formulation comprises a pharmaceutically acceptable carrier or diluent. The formulation disclosed herein can be frozen or lyophilized.

The formulation comprising the purified α-thrombin or homogeneous post-translationally modified α-thrombin can be applied to a surface in a subject. The formulation can be applied with a solution comprising fibrinogen. The formulation may be used, for example, in hemostasis, tissue fixation, graft fixation, wound healing and anastomosis.

In yet another aspect, provided herein is a formulation comprising purified β-thrombin as disclosed herein. In some embodiments, the purified β-thrombin is obtained by the methods disclosed herein. The formulation comprising the purified β-thrombin can be applied to a surface in a subject. The formulation can be applied with a solution comprising fibrinogen. The formulation may be used, for example, in hemostasis, tissue fixation, graft fixation, wound healing and anastomosis.

The term "purified β-thrombin", typically, refers to a β-thrombin preparation obtained following isolation of the β-thrombin from α-thrombin, γ-thrombin and/or another protein present in the starting thrombin comprising solution using an anion exchange chromatography method. By "isolated" it is generally meant, when referring to "isolated homogenous post-translationally modified α-thrombin" or "isolated β-thrombin", that the indicated molecule or compound is separate and discrete from the whole organism with which the molecule or compound is found in nature and/or is sufficiently free of other molecules so that the molecule can be used for its intended purpose.

A "pharmaceutically acceptable carrier or diluent" refers to reagents, compounds, materials, compositions, diluents that are compatible with the constituents in the formulation and suitable for use in contact with the tissues of human beings and animals without excessive toxicity, irritation, allergic response, or other complication commensurate with a reasonable benefit/risk ratio. A pharmaceutically acceptable carrier suitable for use with the formulation disclosed herein can be a liquid, semi-solid and solid material. A carrier may be a sponge, film, plaster, surgical dressing or a bandage.

In another aspect, provided herein is a method for hemostatic treatment, sealing, graft fixation, wound healing, anti-adhesion and/or anastomosis in a subject in need, comprising applying to the subject an effective amount of a formulation according to the invention. The terms "a therapeutically effective amount" or "an effective amount" refer to the dose required to prevent or treat (relieve a symptom or all of the symptoms) a disease, disorder or condition. The effective amount can be measured based on any change in the course of the disease in response to the administration of the formulation. The effective dose can be changed depending on the age and weight of the subject, the disease and its severity (e.g. early or advanced stage) and other factors which can be recognized by the skilled in the art.

In another aspect, provided herein is a method for screening compounds for their potential use in stabilizing thrombin activity in an aqueous liquid thrombin formulation, the method comprising the steps of: incubating test compounds with a solution comprising α-thrombin for a given time; after the incubation, quantifying the α-thrombin and/or the degradation polypeptides (e.g. β-thrombin and/or γ-thrombin polypeptides) according to method disclosed herein; and identifying one or more suitable test compounds which have a potential use in stabilizing thrombin activity, wherein a suitable compound is a compound that maintains the α-thrombin content at a level of about 70% to about 100% compared to the initial α-thrombin content and/or which reduces the level of degradation polypeptides to about 0% to about 30% as compared to the level of degradation polypeptides in the absence of the test compound.

"Stabilizing thrombin activity" refers to, for example, reducing thrombin autolytic activity. "Stabilizing thrombin activity" may also refer to maintaining thrombin activity when stored for more than one day, e.g. at room temperature as an aqueous thrombin solution e.g. a concentrated thrombin solution; more than two years at equal to or less than −18° C.; and/or more than one month at 2-8° C., without significantly compromising thrombin's biological activity towards heterologous substrates, including the activity of conversion of fibrinogen to fibrin. "Room temperature" is meant to include temperature of about 20° C. to about 25°

C., or 22° C. to about 25° C. "Thrombin activity" is meant to include thrombin mediated conversion of heterologous substrates, including proteins e.g. fibrinogen into fibrin, as well as the conversion of Factor VIII to Factor VIIIa, XI to XIa, XIII to XIIIa, and Factor V to Va. A "heterologous substrate" is a substrate, preferably a protein substrate, other than thrombin. In some embodiments, the thrombin activity refers to conversion of fibrinogen into fibrin.

The term "stabilizing" means, for example, maintaining the thrombin activity/potency within the thrombin liquid formulation at a level of about 70% to about 100% (e.g. about 90 to 100%) compared to the initial thrombin activity.

In some embodiments the compound(s) inhibit autolysis of thrombin by about 70% to about 100%, about 70% to about 95%, about 70% to about 90%, or about 70% to about 80%, and retains about 70% to about 100%, about 70% to about 95%, about 70% to about 90%, or about 70% to about 80% thrombin biological activity.

The term "test compounds" or "test substance" is a chemically defined compound or mixture of compounds whose ability to stabilize thrombin is defined by the methods of the invention. These compounds or mixtures of compounds can be any excipient(s)/stabilizers known in the art such as described in Dave A. Parkins and Ulla T. Lashmar "The formulation of biopharmaceutical products". PSTT Vol. 3, No. 4 Apr. 2000.

The term "initial α-thrombin content" refers, for example, to the activity of thrombin towards fibrinogen measured in a thrombin liquid formulation immediately after thawing a frozen thrombin formulation; immediately after reconstituting thrombin powder; and/or before storage of liquid thrombin under conditions that allow self-degradation (e.g. more than two years storage at equal or less than −18° C.; more than one month storage at 2-8° C.; and/or more than 1 day at room temperature e.g. at concentrations of 800 IU/ml to 10,000 IU/ml thrombin or more).

In some embodiments, the incubation time is more than one day (e.g. at room temperature) as an aqueous thrombin solution e.g. a concentrated thrombin solution; more than two years at equal to or less than −18° C.; and/or more than one month at 2-8° C.

The term "degradation polypeptides" refers to β-thrombin and/or γ-thrombin polypeptide.

The term "surface" may refer to an external surface of the skin that can be seen by unaided vision and to a surface of an internal body part which is a part of the internal anatomy of an organism. External surfaces include, but are not limited to, the skin of the face, throat, scalp, chest, back, ears, neck, hand, elbow, hip, knee, and other skin sites. Examples of internal body parts include, but are not limited to, body cavity or anatomical opening that are exposed to the external environment and internal organs such as the nostrils; the lips; the ears; the genital area, including the uterus, vagina and ovaries; the lungs; the anus; the spleen; the liver; and the cardiac muscle. The surface can be a bleeding or a non-bleeding site.

The formulations and kits disclosed herein can be used internally and externally, for tissue and organ graft fixation, for sealing a surgical wound, in vascular surgery including providing hemostasis, for anti-adhesion and for anastomosis such as arterial, gastrointestinal and tracheal anastomosis.

A "subject" as used herein, includes humans and animals of mammalian origin. In one embodiment, a subject is a surgery patient or a wounded patient.

The purified α-thrombin and/or the purified β-thrombin can be used in hemostatic products. The α-thrombin or β-thrombin can be used in combination with fibrinogen to form fibrin sealant.

The fibrinogen can be prepared from initial blood composition. The blood composition can be whole blood or blood fractions, i.e. a product of whole blood such as plasma. In one embodiment of the invention, the fibrinogen component is comprised from a biologically active component (BAC) which is a solution of proteins derived from blood plasma which can further comprise tranexamic acid and/or stabilizers such as arginine, lysine, their pharmaceutically acceptable salts, or mixtures thereof. BAC can be derived from cryoprecipitate, in particular concentrated cryoprecipitate.

The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitate that contains fibrinogen and Factor XIII. The precipitate can be collected, for example by centrifugation and dissolved in a suitable buffer such as a buffer containing 120 mM sodium chloride, 10 mM trisodium citrate, 120 mM glycine, 95 mM arginine hydrochloride. The solution of BAC may comprise further Factor VIII, fibronectin, von Willebrand factor (vWF), vitronectin, etc. for example as described in U.S. Pat. No. 6,121,232 and WO9833533. Preferably, the composition of BAC can comprise stabilizers such as tranexamic acid and arginine hydrochloride. Typically, the amount of fibrinogen in BAC is in the range of from about 40 to about 60 mg/ml. The amount of tranexamic acid in the solution of BAC can be from about 80 to about 110 mg/ml. The amount of arginine hydrochloride can be from about 15 to about 25 mg/ml.

Optionally, the solution is buffered to a physiological compatible pH value. The buffer can be composed of glycine, sodium citrate, sodium chloride, calcium chloride and water for injection as a vehicle. Glycine can be present in the composition in the amount of from about 6 to about 10 mg/ml, the sodium citrate can be in the range of from about 1 to about 5 mg/ml, sodium chloride can be in the range of from about 5 to about 9 mg/ml and calcium chloride can be in the concentration of about 0.1-0.2 mg/ml.

In another embodiment, the concentration of plasminogen and plasmin in the BAC composition is lowered to equal or less than 15 μg/ml like for example 5 μg/ml or less plasminogen using a method as described in U.S. Pat. No. 7,125,569, EP 1,390,485 and WO02095019. In another embodiment of the invention, when the concentration of plasminogen and plasmin in the BAC composition is lowered, the composition does not contain tranexamic acid or aprotinin. The fibrinogen solution may be the BAC2 component (from EVICEL®) or any other fibrinogen containing solution, such as purified recombinant fibrinogen or cryoprecipitate produced from human plasma.

Fibrinogen can be autologous, human including pooled plasma, or of non-human source. It is also possible that the fibrinogen is prepared by recombinant methods or can be chemically modified.

While the following examples demonstrate certain embodiments of the invention, they are not to be interpreted as limiting the scope of the invention, but rather as contributing to a complete description of the invention.

EXAMPLES

For all examples, herein, the following terms are used:

A "thrombin solution" refers to a solution of thrombin at about 3000 IU/ml thrombin, a total protein concentration of about 1 mg/ml, in 20 mM sodium acetate at pH 6.9-7.1.

A "thrombin formulation" or "formulated thrombin" refers to a formulated thrombin drug product EVITHROM® Thrombin, Topical (Human) (ETHICON, Inc.) or the thrombin component of EVICEL® Fibrin Sealant (ETHICON, Inc.), with a thrombin activity in the range of 800-1200 IU/ml, a total protein concentration of about 5.7-6.5 mg/ml, and 5.0 to 6.5 mg/ml human serum albumin (HSA) at pH 6.9-7.1. The HSA used for the formulation of Thrombin includes a stabilizer, acetyltryptophan.

In all experiments below, the thrombin solution was used as a "control sample" which comprises thrombin degradation polypeptides since the thrombin present is not formulated (e.g. does not comprise stabilizers) and highly concentrated (about 3000 IU/ml) and therefore the thrombin is prone to faster degradation (compared to the thrombin present in the "thrombin formulation").

In the following Examples, tools were assessed for their ability to provide separation between α-thrombin, its degradation polypeptides and, if present, HSA, and to quantify α-thrombin and its degradation polypeptides.

In general, "good separation" is considered a "baseline resolution" between the peaks. "Baseline resolution" means an efficient separation of the analytes, in which the peaks detected as representative of elution of the analytes do not overlap; that is, the detector response returns to the base line level between the peaks.

"Sufficient separation"—a clear distinction between the eluting peaks appears, however, the detector response does not fully return to the base line level between the peaks.

Insufficient separation is considered—when overlaps of peaks appear in the chromatogram.

Unless noted with values, the resolution/separation level was visually evaluated. Where numerical values are listed in the Examples below, the resolution ($R_s$), the extent to which a chromatographic column separates components from each other, is mathematically defined as follows: resolution is the difference between the peak retention times of a selected peak and the peak preceding it multiplied by a constant of 1.18, then divided by the sum of the peak widths at 50% of peak height.

A resolution level of equal to or above 2 is considered a "baseline resolution" and therefore shows good separation and allows good quantitation of the peaks. A resolution of equal to or above 1.5 (and lower than 2) is considered "sufficient separation" which enables separation and quantitation.

With regards to the chromatographic method efficacy, the terms "separation" and "resolution" are used interchangeably.

Example 1: Reverse-Phase High-Performance Liquid Chromatography (RP-HPLC) of HSA, Thrombin Solution and Formulated Thrombin A standard procedure for separating proteins and fragments thereof is the employment of HPLC devices in reverse phase mode. The basic principle of the RP-HPLC method is a device, consisting of a dual pump, a polar column, and a detector. The proteins are injected into the device and get retained on the column. Upon increasing the concentration of organic solvents, the proteins and peptides retained on the column are released from the column and elute into the detector, where a response is received based on the amount of proteins eluted at the given time.

In the following Example, a RP-HPLC with a C4 column (Phenomenex, Jupiter, 00G-4167-B0, 4.6×250 mm) was evaluated as a tool to separate between α-thrombin, its degradation polypeptides and, if present, HSA, and to quantify α-thrombin and its degradation polypeptides.

The HPLC analysis was carried out using a Waters Alliance separation module, e2695 with a 100 μL injection loop; a photodiode array (PDA) detector, 2998 (scanning between $A_{190\,nm}$ to $A_{450\,nm}$) was used with an integral Waters column oven at 50° C.

The organic solvents/solutions used for separation were:
Buffer A: HPLC grade water+0.1% (v/v) trifluoroacetic acid (TFA);
Buffer B: acetonitrile+0.1% (v/v) trifluoroacetic acid (TFA).

Different solution gradients (Buffer A and Buffer B ratios over time) were evaluated.

The samples injected were: a) 30 μL thrombin solution; b) 100 μL formulated thrombin; c) 100 μL 5 mg/ml HSA; and d) 100 μL HPLC grade water as a blank sample.

In all the experiments, the different injection volumes were based on the fact that thrombin in the thrombin solution was more concentrated as compared to the formulated thrombin.

Prior to injection, all samples were filtered through a 0.45 μm Polyvinylidene difluoride (PVDF) membrane (Millipore, to filter out larger particles e.g. aggregates). The samples were stored at 10° C. in an integral sample compartment until injected into the HPLC.

Figure 1:
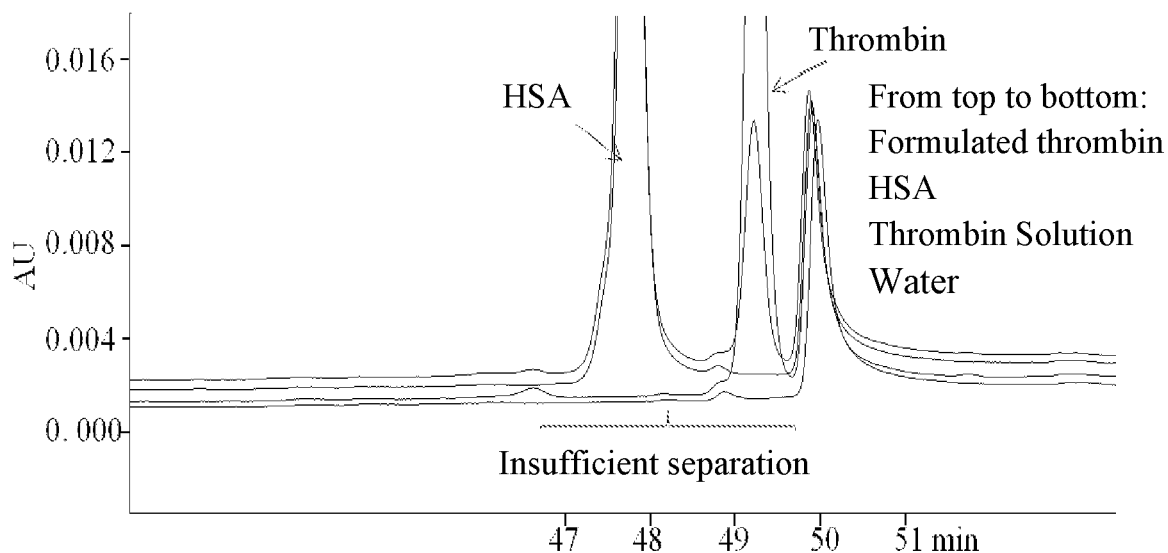
FIG. 1 shows a zoom-in view of a representative chromatogram in the region of the eluting peaks obtained using a Reverse Phase High-Performance Liquid Chromatography (RP-HPLC) of several samples: HSA, thrombin solution, formulated thrombin and water. The samples injected were: a) 30 µL thrombin solution; b) 100 µL formulated thrombin; c) 100 µL 5 mg/ml HSA; and d) 100 µL HPLC grade water as a blank sample.

FIG. 1 shows a zoom-in view of a representative chromatogram in the region of the eluting peaks.

In all Figs. the sample depictions is shown from top to bottom based on the beginning of the chromatogram, the sample injected (from top to bottom) is listed on the chromatogram. The runs of the different samples are shown in one figure as stacked overlays.

Although there was separation between the main peaks of HSA and thrombin, overall not enough separation was achieved. The peaks eluted from the column were too close to allow reliable separation and/or quantitation of the peaks.

Additional experiments were carried out where conditions including temperature, column chemistry (different tested RP columns are listed below), mobile phase chemistry (such as methanol) and gradients were altered, yet the resolution between α-thrombin and its degradation polypeptides and/or other proteins e.g. HSA did not improve.

The following additional RP columns were tested: Cosmosil C4, 5 μm, 300 A, 4.6×250 mm; Sepax BioC18, 3 μm, 300 A, 4.6×150 mm; LiChroCART, 5 μm, 300 A, 4×250 mm; Sepax C8, 5 μm, 300 A, 4×250 mm; Waters XBridge C4, 3.5 μm, 300 A, 4×250 mm for the separation and quantitation as mentioned above.

Therefore it was concluded that, RP-HPLC is not an appropriate tool if a "one-step" or "single column separation" and/or quantitation of α-thrombin in the presence of degradation polypeptides and/or HSA is desired.

Example 2: Anion Exchange High-Performance Liquid Chromatography (AEX-HPLC) and Elution Using a Linear Salt Gradient and pH 8.0

A standard procedure for separating proteins and fragments thereof is the employment of HPLC devices in anion exchange mode. The basic principle of the AEX-HPLC method is a device, consisting of a dual pump, a polar column, and a detector. The proteins are injected into the device and are retained on the column. Upon changing the solvent characteristics (e.g. salt concentration, pH), the proteins and peptides retained on the column are released from the column and elute into the detector, where a response is received based on the amount of proteins eluted at the given time.

In this experiment, HPLC analysis using an anion exchange column was evaluated as a tool to separate between α-thrombin, its degradation polypeptides and, if present, HSA and to quantify α-thrombin and its degradation polypeptides.

AEX-HPLC analysis was carried out using a Waters Alliance separation module, e2695 with a 100 μL injection loop; a PDA detector was used at $A_{220\ nm}$ and $A_{280\ nm}$, and an integral Waters column oven at 25° C. The column used was a Sepax 403NP5-4625 (Sepax Proteomix SAX-NP5 NP 4.6×250 mm 403NP5-4625). The column (4.6 mm width and 250 mm in length) is based on 5 μm polymer beads. The beads have quaternary ammonium chemistry and are non-porous, mono-disperse particles.

For elution from the AEX-HPLC a linear salt gradient between Buffer A: 20 mM Tris pH 8.0 in HPLC grade water; and Buffer B: 20 mM Tris pH 8.0 and 1 M NaCl in HPLC grade water were used.

The samples injected were: a) 30 μL thrombin solution; b) 100 μL formulated thrombin; c) 100 μL 5 mg/ml HSA; and d) 100 μL Buffer A as a blank sample.

Prior to injection, all samples were filtered through a 4 mm syringe filter with 0.45 μm pore size PVDF membrane. The samples were stored at 10° C. in an integral sample compartment until injected into the HPLC. The run time was 37 minutes; the flow rate used was 0.8 mL/min and the pressure was about 2600 psi.

FIG. 2 shows a zoom-in view of a representative chromatogram in the region of the eluting peaks.

The results show that AEX-HPLC with elution buffer at pH 8.0 and linear salt gradient to 1 M NaCl did not provide sufficient separation and/or allow reliable quantitation. The peaks eluted from the column were too close to each other, the resolution was not sufficient.

Example 3: AEX-HPLC and Elution Using a Linear Salt Gradient and pH 6.0

The preceding Example showed that at pH 8.0 and a linear salt gradient, the separation between α-thrombin, its degradation polypeptides and HSA was limited.

In this Example, elution using a phosphate buffer at pH 6.0 with an increasing gradient to 1 M NaCl was evaluated using the column, device and experimental setup as described in Example 2.

For elution from the AEX-HPLC a linear salt gradient between Buffer A: 20 mM phosphate buffer pH 6.0 in HPLC grade water; and Buffer B: 20 mM phosphate buffer pH 6.0 and 1 M NaCl in HPLC grade water were used.

The samples injected were: a) 30 μL thrombin solution; b) 100 μL formulated thrombin; c) 100 μL 5 mg/ml HSA; and d) 100 μL Buffer A as a blank sample.

FIG. 3 shows a representative chromatogram obtained for the different samples.

The results show that AEX-HPLC with elution buffer pH 6.0 and salt gradient to 1 M NaCl did not provide sufficient separation and/or allow reliable quantitation.

Acetyltryptophan seen in the chromatogram is a stabilizer present in the HSA formulation.

Example 4: AEX-HPLC and Elution Using a Linear Salt Gradient and pH 7.5

The preceding Examples showed that the separation was limited using an elution buffer at pH 6.0 (Example 3) and 8.0 (Example 2), and therefore an elution buffer at pH 7.5 was tested.

HPLC analysis and conditions were carried out as described in Example 2. Elution was carried out using a Tris buffer at pH 7.5 with an increasing linear gradient of NaCl. The Buffers used were: Buffer A: 20 mM Tris pH 7.5 in HPLC grade water; and Buffer B: 20 mM Tris pH 7.5 and 1 M NaCl.

The samples injected were: a) 30 μL thrombin solution; b) 100 μL formulated thrombin; c) 100 μL 5 mg/ml HSA; and d) 100 μL Buffer A as a blank sample. Results are shown in FIG. 4 (zoom-in view). The results show that AEX-HPLC with elution buffer pH 7.5 and salt gradient to 1 M NaCl did not provide enough separation and/or allow reliable quantitation.

Example 5: AEX-HPLC and Elution Using a Linear $NaNO_3$ Salt Gradient and pH 8.0

As an alternative to NaCl, $NaNO_3$ (sodium nitrate) was evaluated for its ability to separate thrombin degradation polypeptide from α-thrombin and from the remaining proteins in solution e.g. HSA.

A linear salt gradient was evaluated between Buffer A: 20 mM Tris pH 8.0 in HPLC grade water; and Buffer B: 20 mM Tris pH 8.0/1 M $NaNO_3$. The column, device and experimental setup were as described in Example 2.

The samples injected were: a) 30 μL thrombin solution; b) 100 μL formulated thrombin; and c) 100 μL 5 mg/ml HSA. Results are shown in FIG. 5. As mentioned above, thrombin solution contained degradation polypeptides.

The results show that the use of $NaNO_3$ as an eluent did greatly increase the separation between HSA, acetyltryptophan, and thrombin, however, not sufficient resolution was achieved between thrombin and its degradation polypeptides.

Example 6: AEX-HPLC and Elution Using a Linear Gradient Between pH 9.1 to pH 3.4

As an alternative to using a salt gradient to achieve separation between the relevant peaks eluted from the AEX-HPLC resin, a pH gradient using amine based buffers was evaluated. Due to the amine character of the buffer, the detection was carried out at $A_{280\ nm}$.

Buffers A and B contained: 20 mM piperazine (Sigma Aldrich, P45907), 20 mM triethanolamine (Sigma Aldrich, T9534), 20 mM bis-tris propane (Sigma Aldrich, B4679), and 20 mM 1-methylpiperazine (Sigma Aldrich, 13000-1).

The buffers were adjusted to pH 9.1 (Buffer A) and pH 3.4 (Buffer B) by titration with HCl. Total run time was 46 minutes. In all experiments, a linear gradient was run between steps 2 and 3 (see Table 1 below)—the run time for the linear gradient was 20 minutes. During steps 2 and 3, the materials are eluted from the column.

The samples injected were: a) 30 μL thrombin solution; b) 100 μL formulated thrombin; c) 100 μL 5 mg/ml HSA; and d) 100 μL Buffer A as a blank sample.

Flow conditions and the ratio between the buffers are presented in Table 1. The pH of the eluting buffer is dependent on the ratio between Buffer A and B. In general, a typical HPLC run consists at least of the following steps:

An equilibrated column is loaded with the material (time between steps 1 and 2—"Loading").

Following this step, the material is eluted from the column (between steps 2 and 3—"Linear Gradient"). This can be carried out isocratically (without changing the buffer composition as compared to the Loading and/or equilibration steps) or through a gradient (changing one of the buffer characteristic, e.g. salt concentration, polarity/pH). In this example, elution was carried out using a linear gradient.

In the next step, the column can be regenerated (between steps 3 and 4—"Column regeneration"), meaning that the remaining materials are given additional time at the highest concentration of the changed characteristic (salt concentration, polarity, pH) in order to elute from the column any remaining material.

The last step (between steps 5 and 6—"Column equilibration") is an equilibration step, to allow the column to return to the original state in which the column is suitable for an additional separation The conditions, column and device were as described in Example 2.

TABLE 1

Gradient and flow conditions.

| Step | Time (min) | Flow rate (mL/min) | % Buffer A | % Buffer B |
|---|---|---|---|---|
| 1 | 0.01 | 0.80 | 90.0 | 10.0 |
| 2 | 5.00 | 0.80 | 90.0 | 10.0 |
| 3 | 25.00 | 0.80 | 0.0 | 100.0 |
| 4 | 30.00 | 0.80 | 0.0 | 100.0 |
| 5 | 31.00 | 0.80 | 90.0 | 10.0 |
| 6 | 46.00 | 0.80 | 90.0 | 10.0 |

Between steps 1 and 2-Loading-5 minutes.
Between steps 2 and 3-Linear Gradient-20 minutes. The increment of Buffer B was 4.5% per minute.
Between steps 3 and 4-"Column regeneration"-5 minutes.
Between steps 5 and 6-"Column equilibration"-15 minutes.

In all the Tables below the steps are characterized and numbered in the same manner.

FIG. 6 shows representative chromatograms of the samples injected. FIG. 7 is a zoom-in view of the thrombin eluting region in the chromatogram from FIG. 6.

The results show that good resolution was obtained between HSA, acetyltryptophan, and thrombin. In the described conditions, several thrombin peaks were obtained (best shown in FIG. 6). In the following examples additional parameters were examined to further enhance the resolution of the thrombin peaks.

Example 7: AEX-HPLC and Elution Using a Linear pH Gradient at Different Flow Rates In order to obtain better separation between the different thrombin peaks, different flow rates were evaluated while keeping the temperature (at 25° C. as in Examples 2-7) and the pH gradient constant.

Buffers A and B were the same as in Example 6. The program (see Table 2 below) was operated four times. Each time at a different flow rate: 0.25, 0.5, 0.75, and 1 mL/min. The gradients evaluated are as shown in Table 2 below.

The injected sample was 30 μL thrombin solution for each tested flow rate.

TABLE 2

Gradient and flow conditions.

| Step | Time (min) | % Buffer A | % Buffer B |
|---|---|---|---|
| 1 | 0.01 | 90.0 | 10.0 |
| 2 | 5.00 | 90.0 | 10.0 |
| 3 | 25.00 | 0.0 | 100.0 |
| 4 | 30.00 | 0.0 | 100.0 |
| 5 | 31.00 | 90.0 | 10.0 |
| 6 | 46.00 | 90.0 | 10.0 |

FIG. 8 shows a zoom-in view of the chromatograms of the flow screen carried out.

The separation (visually inspected) between HSA, acetyltryptophan and thrombin was unaffected by the increase in flow rate (data not shown).

It was shown (FIG. 8) that the resolution between α-thrombin and its degradation polypeptides increases with increasing flow rates. The best resolution was achieved at a flow rate of 1.0 mL/min e.g. more peaks are observed.

Example 8: AEX-HPLC and Elution Using a pH Gradient from 100% Buffer A

In this Example the effect of starting the AEX-HPLC method at a higher pH, as compared to the previous Examples, on the separation resolution was evaluated. For this purpose, a pH gradient with 100% Buffer A (see Table 3) was used instead of 90% (as used in Table 2). As a control, the same set of samples were run in the manner described in Table 3, only that in steps 1, 2, 5, and 6 the percentage of Buffer A was 90 and the percentage of Buffer B was 10.

Buffers A and B were the same as in Example 6. Unless written otherwise, the experimental setup was the same as in Example 6.

The resolution between the peaks was visually evaluated. Table 3 shows the gradient and flow rate conditions.

TABLE 3

Gradient and flow conditions.

| Step | Run Time (min) | Flow (mL/min) | % Buffer A | % Buffer B |
|---|---|---|---|---|
| 1 | 0.01 | 1.00 | 100.0 | 0.0 |
| 2 | 5.00 | 1.00 | 100.0 | 0.0 |
| 3 | 27.00 | 1.00 | 0.0 | 100.0 |
| 4 | 32.00 | 1.00 | 0.0 | 100.0 |
| 5 | 33.00 | 1.00 | 100.0 | 0.0 |
| 6 | 48.00 | 1.00 | 100.0 | 0.0 |

The increment of Buffer B was 4.55% per minute.

The results (data not shown) showed that starting the gradient at a higher pH yielded a better resolution for the thrombin peaks. Accordingly, eluting the proteins from the column with a wider pH range will result in a better separation between the peaks.

In the following examples a pH gradient with 100% Buffer A was used.

Example 9: AEX-HPLC and Elution Using a Linear pH Gradient at Increasing Gradient Run Times In order to obtain better separation/resolution between the different thrombin peaks, increasing gradients (i.e. the time increase was between steps 2 and 3), each by five minutes to 51, 56, and 61 minutes total run time, were evaluated as compared to the run time in Example 6 (i.e. the time between steps 2 and 3 increased from 20 to 25, 30 and 35 minutes). A run time of 46 minutes (as in Example 6) was also tested. The resolution was measured between each peak to its preceding peak.

Unless written otherwise, the experimental setup was the same as in Example 8 using the parameters listed in Table 3.

A thrombin solution (30 μL) was injected. Buffers A and B are same as in Example 6. Tables 4, 5, 6 and 7 show the retention time and the resolution achieved at 46, 51, 56, and 61 minutes total run time, respectively. Retention time is the interval between the instant of injection and the detection of the peak apex (the most upper point of the peak) as representative of elution.

TABLE 4

The resolution of the thrombin peaks at 46 minutes total run time.

| Peak Number | Retention Time of the peaks (min) | Resolution |
|---|---|---|
| 1 | 13.091 | |
| 2 | 14.525 | 3.009959 |
| 3 | 15.736 | 2.475773 |
| 4 | 17.171 | 3.529876 |
| 5 | 18.173 | 3.279746 |
| 6 | 19.055 | 3.217816 |
| 7 | 20.337 | 5.087464 |

TABLE 5

The resolution of the thrombin peaks at 51 minutes total run time.

| Peak Number | Retention Time of the peaks (min) | Resolution |
|---|---|---|
| 1 | 12.514 | |
| 2 | 14.313 | 3.293685 |
| 3 | 15.852 | 2.902742 |
| 4 | 17.598 | 4.012924 |
| 5 | 18.852 | 3.893394 |
| 6 | 19.990 | 3.642576 |
| 7 | 21.557 | 5.218836e |

TABLE 6

The resolution of the thrombin peaks at 56 minute stotal run time.

| Peak Number | Retention Time of the peaks (min) | Resolution |
|---|---|---|
| 1 | 13.018 | |
| 2 | 15.130 | 3.116849 |
| 3 | 16.980 | 2.923051 |
| 4 | 18.025 | 1.818590 |
| 5 | 19.050 | 2.188510 |
| 6 | 20.549 | 4.065546 |
| 7 | 21.929 | 3.775590 |
| 8 | 23.792 | 5.461505 |

TABLE 7

The resolution of the thrombin peaks at 61 minutes total run time.

| Peak Number | Retention Time of the peaks (min) | Resolution |
|---|---|---|
| 1 | 10.682 | |
| 2 | 13.480 | 5.056362 |
| 3 | 15.912 | 3.370500 |
| 4 | 18.064 | 3.068171 |
| 5 | 19.292 | 1.846318 |
| 6 | 20.453 | 2.142551 |
| 7 | 22.197 | 4.254319 |
| 8 | 23.824 | 3.981067 |

The results show that at 56 and 61 minutes total run times (a gradient length of 30 and 35 minutes), an additional peak eluting in a region distinct to the thrombin peaks was separated as compared to the shorter run times.

Advantageously, in order to obtain an additional peak eluting in the distinct thrombin region, a gradient length of higher than 25 minutes may be used.

In the next Examples, a total run time of 56 minutes was used.

Example 10: The Effect of the Linear Gradient Slope on the Separation Resolution Different linear slope gradients were evaluated for their ability to improve separation of thrombin peaks (gradients used between steps 2 and 3). The slope is impacted by the increment of the percentage of Buffer B per minute. A lower increase of the percentage of Buffer B per minute results in a shallower slope as compared to a higher increase of the percentage of Buffer B per minute, thereby affecting the elution profile of the proteins. Contrary to Example 8 in which the gradient was impacted by using a different starting pH, in this Example, the gradient was impacted by incrementing the pH value at different rates per minute (the pH of the start and endpoint are equal in all samples).

Buffers A and B were the same as in Example 6. Unless written otherwise, the experimental setup was the same as in Example 6. A thrombin solution (30 μL) was injected. Buffer A (30 μL) was used as blank (not shown).

The percentages increase of Buffer B per minute evaluated were: 4.5%, 4.25%, 4%, 3.75%, and 3.5%. For example, when a percentage of 4.5% per minute was used, following the first minute 4.5% Buffer B per minute was obtained, following the second minute 9% Buffer B per minute was obtained, following the third minute 13.5% Buffer B per minute was obtained etc. up to 100% Buffer B per minute. At each minute Buffer A was used to complete the total solution to 100%.

Typically, a shallower slope results in an increased run time. The run times were as follows: 48, 49.5, 51, 52.7, and 54.6 minutes, respectively to the listed Buffer B percentage.

FIG. 9 shows the chromatogram obtained for the different gradients evaluated, a visual inspection was carried out to determine the separation resolution.

The results show that all tested slopes showed satisfactory/sufficient separation between thrombin peaks with an increment of 3.5% having the best separation (seen in zoom-in view, data not shown).

Example 11: Identification of the Different Thrombin Peaks by Injection of Commercial Standards in AEX-HPLC In order to identify the thrombin peaks in the chromatogram, a thrombin solution was run as in Example 7 in addition to α, β and γ thrombin standards using a flow rate of 1.0 mL/min.

Standards (Haematological Industries; Human alpha-Thrombin, HTI HCT-0020, Human beta-Thrombin, HTI-0022, Human gamma-Thrombin, HTI-0021) were diluted to 0.3 mg/mL before injection. 30 μL thrombin solution, 100 μL of each α-, β- and γ-standards were injected into the HPLC. Buffer A used as blank.

Buffers A and B were the same as described in Example 7 and used in the program shown in Table 2.

FIG. 10 shows the overlaid chromatograms. Based on the peaks obtained for the standards, it was possible to identify the correlating peaks of the thrombin solution and thereby verify that separation between α-thrombin and its degradation polypeptides β and γ thrombin can be achieved. In addition, it was noted that the α-thrombin elutes as multiple peaks in the chromatogram.

Example 12: Thrombin Peaks Identification Using Western Blot as a Qualitative Tool In the previous Example thrombin peaks identification was carried out by injection of commercial α, β and γ thrombin standards in AEX-HPLC.

To corroborate the above results, in this Example thrombin peaks were collected from an injected thrombin solution and further qualitatively identified by Western Blot against commercial standards (as in Example 11) based on the known size of α-thrombin and its degradation polypeptides, β- and γ-thrombin.

In order to obtain sufficient amounts of β and γ thrombin, a thrombin solution was incubated under conditions that enhance auto-degradation of thrombin such as overnight for at least 12 hours at room temperature (about 20-25° C.) before injection into the HPLC. The experimental setup was as in Example 10, the 3.5% B/min increase was used. 60 μL of the sample (in tetraplicates) and 100 μL Buffer A were injected.

The distinct peaks (shown and identified in FIG. 11 and Table 8) were collected from the four separate runs (due to the small protein amount present in each peak), pooled (according to visual identification and retention time) and lyophilized due to the large collection volume. Each lyophilized pooled peak was reconstituted (in a lower volume of water as compared to the initial volume due to the limitations in the possible load volume of the SDS-PAGE). The resulting pooled samples were separated by SDS-PAGE, transferred onto a nitrocellulose sheet and immune-blotted against polyclonal anti-α-thrombin (data not shown). A mixture of α, β, γ was used as control.

The peaks were identified based on the molecular weights of the bands obtained in the Western Blot and by comparison to the standard α, β, γ mix.

TABLE 8

Peaks collected following injection of a thrombin solution.

| Peak Number | Retention time of the peak (min) | Identification |
|---|---|---|
| 1 | 15.80 to 16.51 | α-thrombin |
| 2 | 17.20 to 18.20 | α-thrombin |
| 3 | 18.55 to 19.00 | β-thrombin |
| 4 | 19.00 to 19.50 | α-thrombin |
| 5 | 20.00 to 20.53 | β and γ-thrombin |
| 5a | 20.53 to 20.7 | β and γ-thrombin |
| 6 | 21.00 to 21.22 | α-thrombin |
| 7 | 21.9 | unidentified |
| 8 | 22.20 to 22.40 | α-thrombin |
| 9 | | unidentified |
| 10 | | unidentified |

The results obtained in the Western Blot show that degradation polypeptides of thrombin elute in peaks 3, 5 and 5a. Peaks 1, 2, 4, 6, and 8 having similar molecular weight, were identified as α-thrombin. The relative area of the peaks labeled as "unidentified" were small compared to the "identified" peaks.

Without being bound by the mechanism, α-thrombin is separated into several peaks in the HPLC-AEX system and probably corresponds to several α-thrombin species differing in their net charge.

The results of Examples 11 and 12 show that advantageously complete separation between α, β, γ-thrombin, α-thrombin species and HSA (data of HSA separation is not shown in this Example) can be obtained using an AEX-HPLC linear pH gradient between 100% Buffer A to 100% Buffer B with a slope of 3.5% Buffer B per minute. Buffer compositions are as described in Example 6.

Example 13: Identification of α-Thrombin Species Resolved by HPLC-AEX

The objective of the present Example was to characterize the multiple peaks detected for α-thrombin in HPLC-AEX chromatography. It was explored if the different species of α-thrombin are due to different post translated modified α-thrombin forms. There are several post-translation modifications; glycosylation is one possibility. Since glycosylation affects the activity of proteins (Ricardo J. Sola and Kai Griebenow. "Glycosylation of Therapeutic Proteins: An Effective Strategy to Optimize Efficacy". BioDrugs. 2010; 24(1): 9-21), the following Example focuses on glycosylation.

Human α-thrombin has a single N-linked glycosylation site on its "heavy chain". It was explored a possibility that the α-thrombin resolved in HPLC-AEX chromatography correspond to α-thrombin containing different sialylation levels on the N-linked glycosylation site i.e. variable amounts of N-acetylneuraminic acid (NANA) (sialic acid) in the glycosylation site.

For this purpose, a thrombin solution was subjected to N-acetylneuraminidase treatment according to manufacturer's instructions (Sigma Aldrich, N2876). N-acetylneuraminidase (NANase) is an enzyme capable of removing the NANA residues from the terminal end of glycans. By removal of these charged sugar residues, the overall charge of each of the glycosylated proteins is brought to the same level.

In the next step, the NANase-treated thrombin solution was injected to an AEX-HPLC system as described in Example 12. Thrombin solution without treatment was injected as control.

The results (FIG. 12) show that treatment of thrombin with NANase affects the elution profile resulting in an overall shift of the peaks to the left side of the chromatogram (as compared to the un-treated thrombin solution). Due to the loss of the negative charge of the sialic acid residue, the protein net charge of thrombin at a given pH is increased, thereby causing an earlier elution from the column. In view of these results, it can be concluded that the numerous peaks results from differences in NANA content.

Example 14: Purifying Homogenously Post-Translationally Modified α-Thrombin from a Proteinatious Solution In the previous Examples it was found that α-thrombin can be resolved into distinct peaks containing different amounts NANA/sialylation level.

In this example, the purpose was to isolate a homogenous α-thrombin species containing a substantially identical profile of NANA using AEX-HPLC. The following conditions were used:

The column used was a Sepax 403NP5-4625, width: 4.6×length: 250 mm as in Example 2. 30 μL of thrombin solution, 100 μL formulated thrombin and 100 μL of Buffer A (not shown) were injected.

Elution of proteins from the resin was carried out using a pH gradient composed of 20 mM piperazine (Sigma Aldrich, P45907), 20 mM triethanolamine (Sigma Aldrich, T9534), 20 mM bis-tris propane (Sigma Aldrich, B4679), and 20 mM 1-methylpiperazine (Sigma Aldrich, 13000-1). The buffers were adjusted to pH 9.1 (Buffer A) and pH 3.4 (Buffer B).

A linear pH gradient, with an increment of 3.5% Buffer B per minute, and flow conditions as shown in Table 9 were used.

TABLE 9

Gradient and flow conditions.

| Step | Run Time (min) | Flow (mL/min) | % Buffer A | % Buffer B |
| --- | --- | --- | --- | --- |
| 1 | 0.01 | 1.00 | 100.0 | 0.0 |
| 2 | 5.00 | 1.00 | 100.0 | 0.0 |
| 3 | 33.60 | 1.00 | 0.0 | 100.0 |
| 4 | 38.60 | 1.00 | 0.0 | 100.0 |
| 5 | 39.60 | 1.00 | 100.0 | 0.0 |
| 6 | 54.60 | 1.00 | 100.0 | 0.0 |

FIG. 13 shows the full length chromatogram of the two eluted thrombin samples. FIG. 14 shows a zoom-in view of the α-thrombin species and the degradation polypeptides eluting region.

For the formulated thrombin chromatogram it can be seen that complete separation between HSA, several charged α-thrombin species (shown with arrows) and acetyltryptophan can be achieved.

For the thrombin solution chromatogram it can be seen that complete separation between several charged α-thrombin species (shown with arrows) and degradation polypeptides can be achieved.

These results show that different homogenous α-thrombin species can be separated from each other in a thrombin containing sample. Also, the results show that the quality of the separation enables to purify homogenously post-translational modified α-thrombin from a proteinatious solution and/or a solution comprising heterogeneously post-translational modified α-thrombin.

Example 15: Quantifying Homogenously Post-Translationally Modified α-Thrombin and Thrombin Degradation Polypeptides The preceding examples show that α-thrombin peaks containing homogenous content of NANA can be well separated by the AEX-HPLC. Complete separation of peaks allows quantitation of α, β, γ thrombin variants in a thrombin containing solution by calculating the integration of a relevant separated peak—see table 10. The conditions used in the AEX-HPLC were as described in the previous Example.

TABLE 10

Quantitation of the different thrombin variants.

| Identification | Retention Time of the peak (min) | Area* | Area (%)** |
| --- | --- | --- | --- |
| α-thrombin | 16.062 | 219077 | 6.72 |
| α-thrombin | 17.698 | 2303906 | 70.65 |
| β-thrombin | 18.717 | 119346 | 3.66 |
| α-thrombin | 19.230 | 273402 | 8.38 |
| β and γ-thrombin | 20.146 | 177410 | 5.44 |
| α-thrombin | 21.000 | 62339 | 1.91 |
| unidentified | 21.543 | 5349 | 0.16 |
| α-thrombin | 22.157 | 87076 | 2.67 |
| unidentified | 24.008 | 8456 | 0.26 |
| unidentified | 24.939 | 4556 | 0.14 |

*Area refers to the integrated area under the peak calculated by the software.
**The relative area from the total calculated peak area.

It was shown that quantification of all α-thrombin species and of the degradation polypeptide was obtained.

The method can advantageously also be used to quantitate the amount of α-thrombin from all proteins present in the solution and/or for screening of suitable formulation.

Also, the results show that one type of β-thrombin can be purified and quantified using the method of the invention.

Although various embodiments have been described herein, many modifications and variations to those embodiments may be implemented. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Citation or identification of any reference in this application shall not be construed as an admission that such reference is available as prior art to the invention.

Section headings are used herein to ease understanding of the specification and should not be construed as necessarily limiting.

The invention claimed is:

1. A solution comprising: homogenous post-translationally modified α-thrombin, and an eluent comprising a mixture of amines, wherein the isolated homogenous post-translationally modified α-thrombin is homogeneously sialylated α-thrombin.

2. The solution of claim 1, wherein the α-thrombin is from a human plasma source.

3. The solution of claim 1, wherein the homogenous post-translationally modified α-thrombin is homogeneously glycosylated α-thrombin.

4. The solution of claim 1, wherein the α-thrombin is represented by one particular glycoform.

* * * * *